US009803014B2

(12) United States Patent
Imhof et al.

(10) Patent No.: US 9,803,014 B2
(45) Date of Patent: Oct. 31, 2017

(54) JAM-C ANTIBODIES AND METHODS FOR TREATMENT OF CANCER

(71) Applicant: Research Development Foundation, Carson City, NV (US)

(72) Inventors: Beat Imhof, Geneva (CH); Christiane Ody, Geneva (CH); Thomas Matthes, Geneva (CH); Carmen Donate, Geneva (CH)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 14/438,505

(22) PCT Filed: Oct. 24, 2013

(86) PCT No.: PCT/US2013/066534
§ 371 (c)(1),
(2) Date: Apr. 24, 2015

(87) PCT Pub. No.: WO2014/066590
PCT Pub. Date: May 1, 2014

(65) Prior Publication Data
US 2015/0246971 A1    Sep. 3, 2015

Related U.S. Application Data

(60) Provisional application No. 61/717,796, filed on Oct. 24, 2012, provisional application No. 61/773,933, filed on Mar. 7, 2013.

(51) Int. Cl.
| | |
|---|---|
| *C07K 16/28* | (2006.01) |
| *G01N 33/574* | (2006.01) |
| *A61K 47/48* | (2006.01) |
| *C07K 16/30* | (2006.01) |
| *A61K 39/00* | (2006.01) |
| *A61K 45/06* | (2006.01) |

(52) U.S. Cl.
CPC .......... *C07K 16/2803* (2013.01); *A61K 45/06* (2013.01); *A61K 47/4863* (2013.01); *C07K 16/2842* (2013.01); *C07K 16/3061* (2013.01); *G01N 33/57426* (2013.01); *A61K 2039/505* (2013.01); *A61K 2039/507* (2013.01); *C07K 2317/73* (2013.01); *C07K 2317/76* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,001,225 A * | 3/1991 | Taylor ............. | A61K 47/48507 424/131.1 |
| 7,642,341 B2 | 1/2010 | Imhof et al. | |
| 7,790,863 B2 | 9/2010 | Imhof et al. | |
| 8,007,797 B2 | 8/2011 | Dietrich et al. | |
| 8,093,010 B2 | 1/2012 | Imhof et al. | |
| 2004/0180002 A1* | 9/2004 | Young ............... | C07K 16/00 424/1.49 |
| 2004/0197328 A1* | 10/2004 | Young ............ | A61K 47/48569 424/141.1 |
| 2006/0171952 A1 | 8/2006 | Mather et al. | |
| 2007/0202110 A1* | 8/2007 | Imhof ............... | C07K 16/2803 424/155.1 |

FOREIGN PATENT DOCUMENTS

| | | |
|---|---|---|
| EP | 1533617 | 5/2005 |
| WO | WO 2005/050213 | 6/2005 |
| WO | WO 2008/038127 | 4/2008 |

OTHER PUBLICATIONS

Ody et al. (Haemtologica Jun. 1, 2011 96 (Suppl. 2): 143, Abs. No. 0343).*
Harlow and Lane (Antibodies, a Laboratory Manual, Cold Spring Harbor Laboratory Press, 1988, pp. 141-142).*
Gura (Science, 1997, 278:1041-1042).*
Kaiser (Science, 2006, 313: 1370).*
Gerdes et al. (Front. Oncol. Dec. 18, 2014 doi: 10.3389/fonc.2014. 00366, pp. 1-12).*
Rudikoff et al. (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Gussow et al. (1991, Methods in Enzymology 203:99-121).*
Engraftment (Medical dictionary http://medical-dictionary. thefreedictionary.com/engraftment, downloaded Feb. 10, 2017).*
Arcangeli et al., "The junctional adhesion molecule-B regulates JAM-C-dependent melanoma cell metastasis," *FEBS Letters*, 586(22):4046-4051, 2012.
Aurrand-Lions et al., "JAM-2, a novel immunoglobulin superfamily molecule, expressed by endothelial and lymphatic cells," *Journal of Biological Chemistry*, 276(4):2733-2741, 2001.
Donate et al., "Homing of human B cells to lymphoid organs and B-cell lymphoma engraftment are controlled by cell adhesion molecule JAM-C," *Cancer Research*, 73(2):640-651, 2013.
Fuse et al., "Junctional adhesion molecule-C promotes metastatic potential of HT1080 human fibrosarcoma," *Journal of Biological Chemistry*, 282(11):8276-8283, 2007.
Ody et al., "Junctional adhesion molecule C (JAM-C) distinguishes CD27+ germinal center B lymphocytes from non-germinal center cells and constitutes a new diagnostic tool for B-cell malignancies," *Leukemia*, 21(6):1285-1293, 2007.
PCT International Preliminary Report on Patentability issued in International Application No. PCT/US2013/066534, mailed May 7, 2015.

(Continued)

*Primary Examiner* — Peter J Reddig
(74) *Attorney, Agent, or Firm* — Parker Highlander PLLC

(57) ABSTRACT

A novel method to reduce B-cell lymphoma cell migration to and engraftment of the spleen in patients with JAM-C positive B-cell lymphomas is described. In certain aspects, a method for identifying and treating JAM-C positive B-cell lymphoma patients with anti-JAM-C antibodies is provided. Recombinant antibody molecules that specifically bind to JAM-C are also disclosed.

12 Claims, 25 Drawing Sheets

(56) References Cited

OTHER PUBLICATIONS

PCT International Search Report and Written Opinion issued in International Application No. PCT/US2013/066534, mailed Dec. 17, 2013.
Donate et al., "Junctional adhesion molecule C (JAM-C) influences selectively the homing of normal and malignant B-cells to different lymphoid organs," Poster, 2011.

* cited by examiner

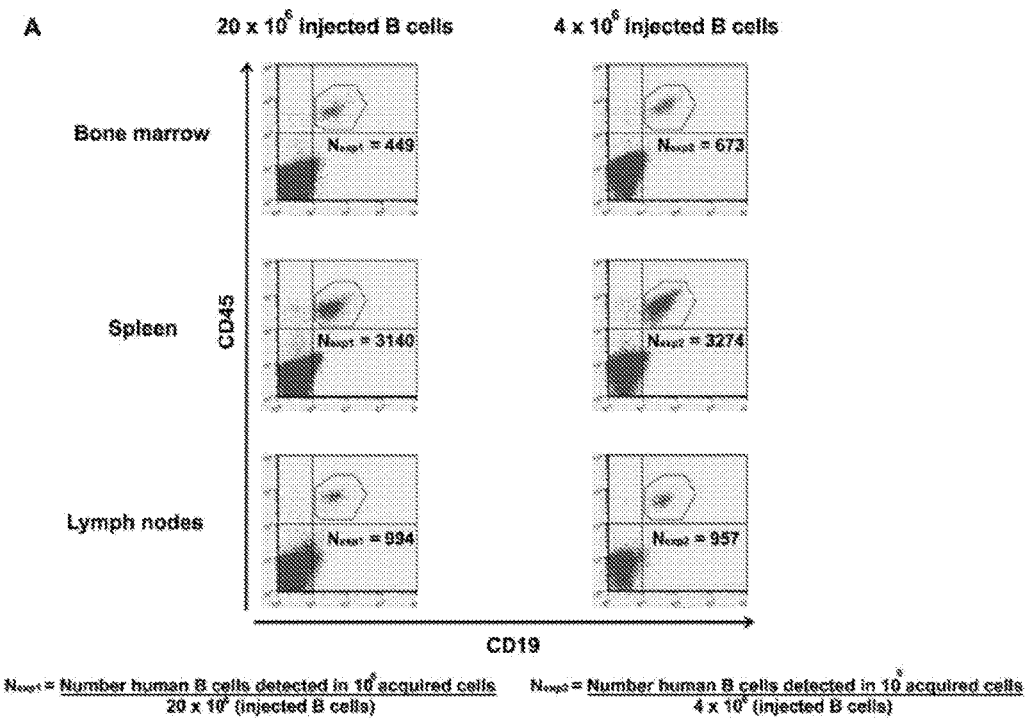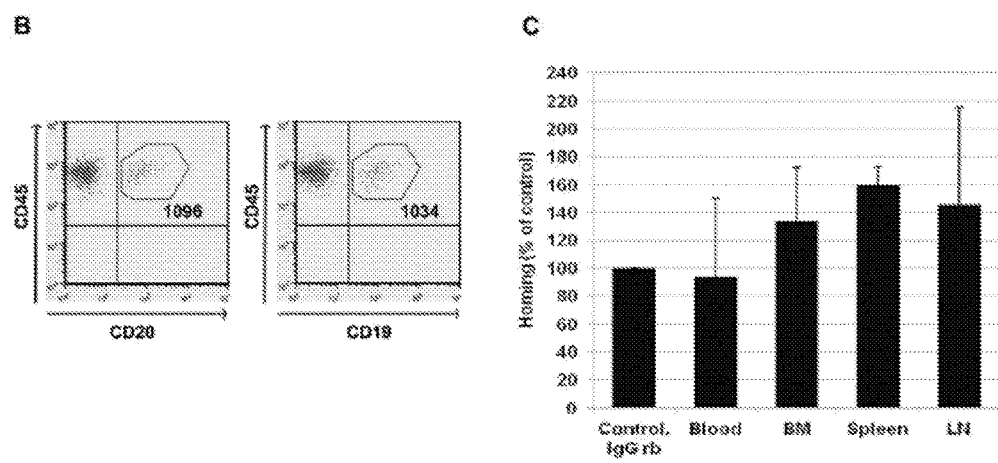
FIGs. 8A-C

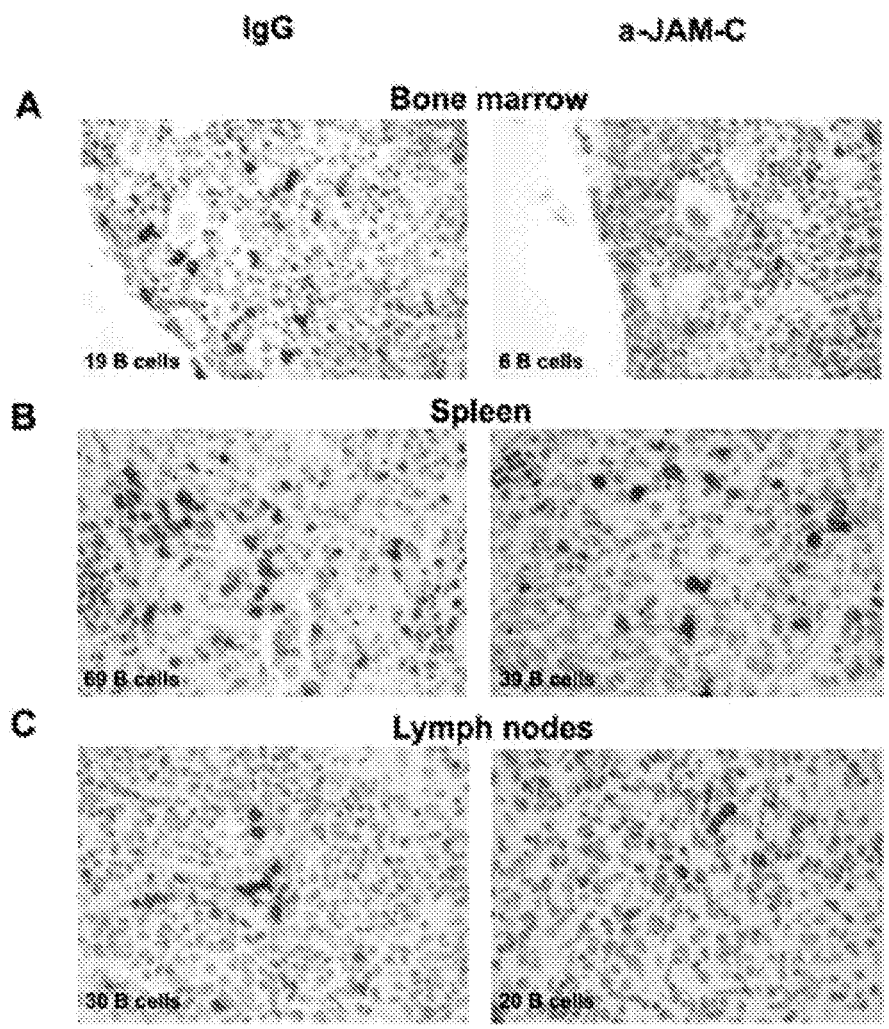
FIGs. 9A-C

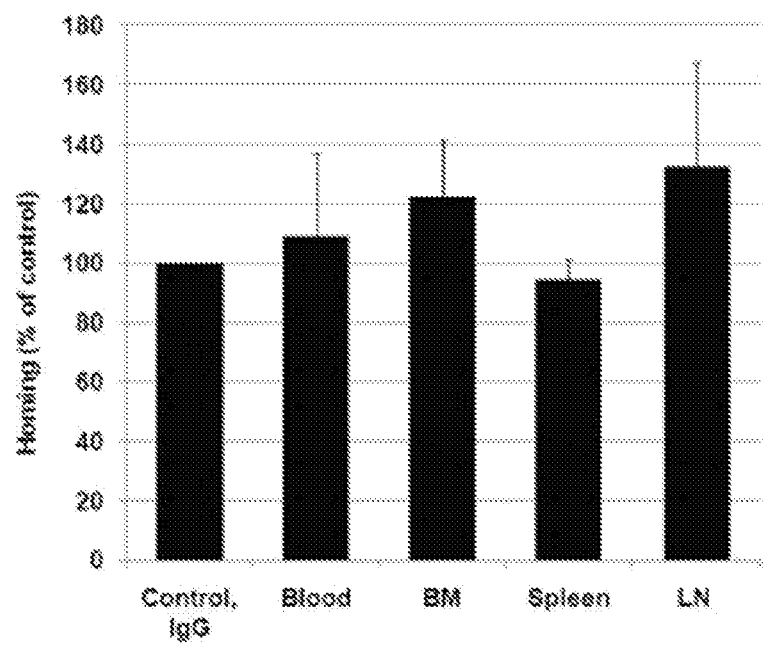
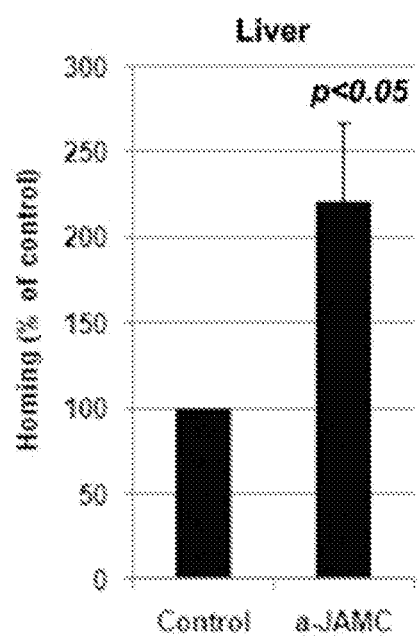
FIGs. 12A-B

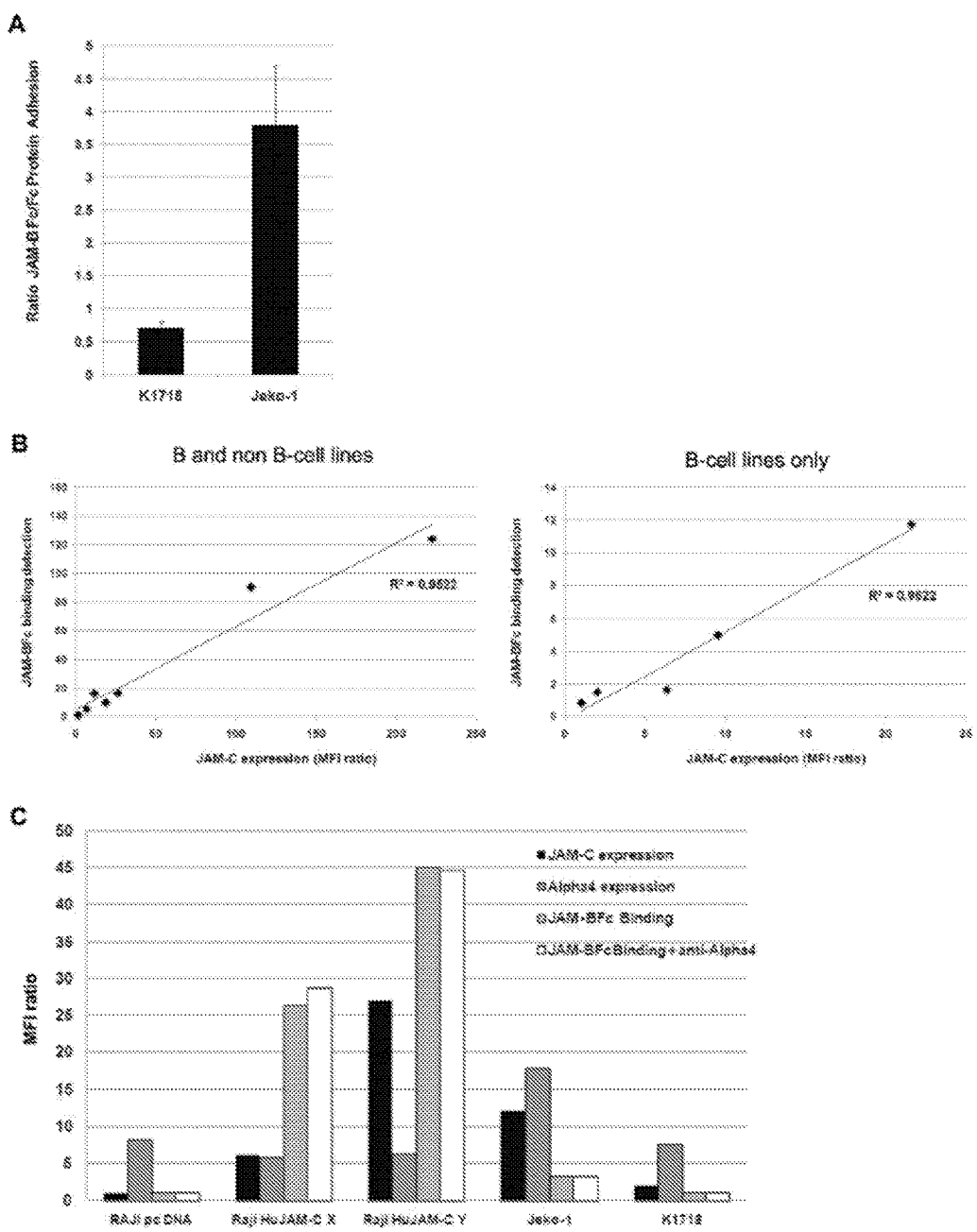
FIGs. 13A-C

JAM-C ANTIBODIES AND METHODS FOR TREATMENT OF CANCER

The present application is a national phase application under 35 U.S.C. §371 of International Application No. PCT/US2013/066534, filed Oct. 24, 2013, which claims the priority benefit of U.S. provisional application Nos. 61/717,796, filed Oct. 24, 2012 and 61/773,933, filed Mar. 7, 2013, the entire contents of each of which are incorporated herein by reference.

The sequence listing that is contained in the file named "CLFRP0402US.txt", which is ~19 KB (as measured in Microsoft Windows®) and was created on Apr. 21, 2015, is filed herewith by electronic submission and is incorporated by reference herein.

BACKGROUND OF THE INVENTION

1. Field of the Invention

The present invention relates generally to the fields of molecular biology, hematology and oncology. More particularly, it concerns JAM-C-targeted antibodies and therapies and anti-cancer therapies with such antibodies.

2. Description of Related Art

Despite new treatment strategies, most mature B-cell lymphomas remain incurable. Evidence suggests that stromal cells in specialized tissue microenvironments, such as bone marrow (BM) and secondary lymphoid organs, are essential for disease progression. In fact, contact with stromal cells and the cytokines secreted by them favor viability, differentiation, proliferation, and retention of B cells and provide protection from conventional chemotherapy (Bertrand et al., 2000; Burger et al., 2009).

To enter lymphoid organs, B cells must adhere to endothelium and transmigrate across the endothelial barrier, thus chemokines and adhesion molecules are important in the homing of normal and malignant B cells and in lymphoma dissemination (Hartmann et al., 2009; Jin et al., 2006; Luster et al., 2005; Matsunaga et al., 2003; Mori et al., 2004; Okada and Cyster, 2006; Spiegel et al., 2004; Tavor et al., 2004). Both firm adhesion and transmigration across endothelial barriers depend on the ability of circulating cells to interact with endothelium through selectin ligands, integrins, or CD44. However, except CD44, these molecules are not involved in homing to the spleen.

Homing of circulating lymphocytes to secondary lymphoid organs is a multistep process, involving engagement of L-selectin, which mediates lymphocyte rolling along the luminal surface of HEVs, followed by activation of lymphocyte integrins and transmigration through the endothelial cell layer. Once inside lymphatic tissues, B and T lymphocytes migrate toward specific microenvironments, such as B-cell follicles and the paracortex, respectively. As HEVs are absent in spleen, lymphocytes enter this organ via the terminal branches of the central arterioles, which guide them into the marginal zone (Kraal et al., 1995; Miyasaka and Tanaka, 2004). In the bone marrow, migration of hematopoietic cells has been less well studied, although it is known that selectins and integrins are involved in homing to this organ (Cyster, 2003; Papayannopoulou, 2003) and that peripheral B lymphocytes enter through capillaries. Similar to normal B cells, the migration of malignant cells to specific lymphoid microenvironments constitutes a central aspect of B-cell lymphoma pathophysiology, and preventing lymphoma cells from reaching survival niches is important to stop tumor cell proliferation (Burger et al., 2009; Coupland, 2011).

It has been previously reported that B-cell homing to the spleen is integrin-independent, and that incubation of B cells with anti-alpha-4 integrin antibodies reduces homing only to BM and LNs (Hartmann et al., 2009; Lo et al., 2003; Koni et al., 2001; Berlin-Rufenach et al., 1999). Therefore, a new method to block homing of B cells to the spleen is needed.

SUMMARY OF THE INVENTION

It has been discovered that proteins that bind JAM-C have the surprising ability to prevent B-cell lymphoma migration and engraftment to lymphoid tissue, especially the spleen. Lymphoma migration to the spleen causes diffuse splenic infiltration and splenomegaly, which are serious medical conditions associated with many B-cell lymphomas. In certain embodiments, the present invention provides JAM-C-binding polypeptides. The ability of JAM-C-binding proteins to prevent or reduce B-cell lymphoma seeding of the spleen is considered a major medical advance. Therefore, in other aspects of the present invention, there is provided a method for reducing B-cell lymphoma migration to and/or seeding of lymphoid tissue in a patient having a JAM-C positive B-cell lymphoma comprising administering an amount of a JAM-C-binding protein effective to reduce migration to and engraftment of the patient's lymphoid tissue by B-cell lymphoma cells. As used herein, lymphoid tissues include bone marrow, lymph nodes, and the spleen. In certain embodiments, the preferred lymphoid tissue is the spleen.

In accordance with certain aspects of the present invention, there is provided a method for treating JAM-C positive B-cell lymphoma comprising administering an amount of a JAM-C-binding antibody effective to treat the B-cell lymphoma of the patient. In some aspects, a method comprises treating a patient who either has previously been determined to have a JAM-C positive B-cell lymphoma or is determined to have a JAM-C positive B-cell lymphoma.

In certain embodiments, the JAM-C-binding protein may be an antibody, which may be a monoclonal antibody, a polyclonal antibody, a chimeric antibody, an affinity matured antibody, a humanized antibody, a human antibody, or an antigen-binding antibody fragment. Preferably, the antibody is a monoclonal antibody or a humanized antibody. In embodiments where the antibody is an antibody fragment, preferred fragments include Fab, Fab', Fab'-SH, F(ab')$_2$, or scFv molecules.

In another embodiment, the JAM-C-binding protein is a JAM-B polypeptide. For example, the JAM-B polypeptide may be a soluble JAM-B polypeptide (e.g., amino acids 1-238 of NCBI accession number NP_067042.1; SEQ ID NO: 3). Such a polypeptide may be produced recombinantly (see e.g., U.S. Patent Publn. 2005/0136060, which is incorporated herein by reference).

For certain medical or clinical applications, the antibody may be attached to an agent to be targeted to a JAM-C-expressing cell. The agent may be a cytotoxic agent, a cytokine, an anti-angiogenic agent, a chemotherapeutic agent, a diagnostic agent, an imaging agent, a radioisotope, a pro-apoptosis agent, an enzyme, a hormone, a growth factor, a peptide, a protein, an antibiotic, an antibody, a Fab fragment of an antibody, an antigen, a survival factor, an anti-apoptotic agent, a hormone antagonist, a virus, a bacteriophage, a bacterium, a liposome, a microparticle, a magnetic bead, a microdevice, a cell, a nucleic acid, or an expression vector. Where the targeted molecule is a protein, the coding regions for the respective protein molecule and antibody may be aligned in frame to permit the production of a "fused" molecule where desired. In other embodiments, however, the antibody may be conjugated to the molecule using conventional conjugation techniques.

Also contemplated is a method of identifying a lymphoma patient who is a candidate for JAM-C treatment, comprising determining whether the lymphoma is a JAM-C positive B-cell lymphoma, wherein if the lymphoma is a JAM-C positive lymphoma then the patient is a candidate for a JAM-C-targeted therapy. An exemplary means of carrying out such a determination will involve simply obtaining a sample of the lymphoma, such as might be obtained from the patient's blood or a biopsy of an involved organ or lymph node, and conducting an immunological analysis using, for example, anti-JAM-C antibodies. It is contemplated that such an analysis can be carried out using any acceptable immunological detection technique, such as Western blot, ELISA, flow cytometry, and the like. In certain embodiments, the method will further comprise reporting that the patient is a candidate for JAM-C-targeted therapy. Typically such reports are provided to a health care provider, such as a hospital, physician, or the like.

In some embodiments, the present invention is directed towards an isolated or recombinant monoclonal antibody that specifically binds to a JAM-C polypeptide. In certain aspects, an antibody competes for the binding of a JAM-C polypeptide with the H225, Hj223.3, Hj20 or Hj41.5 monoclonal antibody. Preferred antibodies compete for binding of the JAM-C polypeptide with the H225 or Hj223.3 monoclonal antibodies. In certain aspects, the antibody may comprise all or part of the heavy chain variable region and/or the light chain variable region of the H225, Hj223.3, Hj20 or Hj41.5 monoclonal antibodies. In a further aspect, the antibody may comprise an amino acid sequence that corresponds to a first, second, and/or third complementarity determining region (CDR) from the light variable and/or heavy variable chain of the H225, Hj223.3, Hj20 or Hj41.5 monoclonal antibodies of the present embodiments.

In certain aspects, the isolated antibody comprises CDR sequences at least 80%, 90% or 95% identical to the CDR regions of the H225, Hj223.3, Hj20 or Hj41.5 heavy and light chain amino acid sequences. In further aspects, an antibody comprises CDR regions identical to the H225, Hj223.3, Hj20 or Hj41.5, except for one or two amino acid substitutions, deletions or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of a H225, Hj223.3, Hj20 or Hj41.5 monoclonal antibody. Thus, in some specific aspects, an antibody of the embodiments comprises (a) a first VH CDR at least 80% identical to VH CDR1 of H225 (SEQ ID NO: 12), Hj223.3 (SEQ ID NO: 24), Hj20 (SEQ ID NO: 18), or Hj41.5 (SEQ ID NO: 24); (b) a second VH CDR at least 80% identical to VH CDR2 of H225 (SEQ ID NO: 13), Hj223.3 (SEQ ID NO: 13), Hj20 (SEQ ID NO: 19), or Hj41.5 (SEQ ID NO: 26); (c) a third VH CDR at least 80% identical to VH CDR3 of H225 (SEQ ID NO: 14); Hj223.3 (SEQ ID NO: 25), Hj20 (SEQ ID NO: 20), or Hj41.5 (SEQ ID NO: 27); (d) a first VL CDR at least 80% identical to VL CDR1 of H225 (SEQ ID NO: 15), Hj223.3 (SEQ ID NO: 15), Hj20 (SEQ ID NO: 21), or Hj41.5 (SEQ ID NO: 28); (e) a second VL CDR at least 80% identical to VL CDR2 of H225 (SEQ ID NO: 16), Hj223.3 (SEQ ID NO: 16), Hj20 (SEQ ID NO: 22), or Hj41.5 (SEQ ID NO: 29); and (f) a third VL CDR at least 80% identical to VL CDR3 of H225 (SEQ ID NO: 17), Hj223.3 (SEQ ID NO: 17), Hj20 (SEQ ID NO: 23), or Hj41.5 (SEQ ID NO: 30).

In further aspects, the isolated antibody comprises CDR sequences at least 80%, 90% or 95% identify to the CDR regions of the H225, Hj20 or Hj223.3 heavy and light chain amino acid sequences. In further aspects, an antibody comprises CDR regions identical to the H225, Hj20 or Hj223.3 antibody, except for one or two amino acid substitutions, deletions or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of a H225, Hj20 or Hj223.3. For example, in some aspects, a substitution in a CDR from a H225 antibody can be made with the corresponding amino acid position from a CDR of the Hj223.3 or vice versa. Thus, in some aspects, an antibody comprises a $V_H$ CDR1 having the sequence GYTFTSX$_1$X$_2$ (SEQ ID NO: 31), wherein X$_1$ is Phe, Tyr or Trp, preferably Phe or Tyr and wherein X$_2$ is Tyr or Asp; a $V_H$ CDR2 having the sequence of IX$_3$X$_4$GX$_5$GX$_6$T (SEQ ID NO: 32), wherein X$_3$ is Asn or Tyr, X$_4$ Thr or Pro; X$_5$ is Ser or Asn; and X$_6$ is Gly or Asn (e.g., SEQ ID NO: 13 or 19); a $V_H$ CDR3 having the sequence of ARDNSGYVLDY (SEQ ID NO: 14), ARGDGVDY (SEQ ID NO: 20) or ARDEDTTPFDY (SEQ ID NO: 25); a $V_L$ CDR1 having the sequence QNINX$_7$Y (SEQ ID NO: 33) wherein X$_7$ is Arg, His or Lys, preferably Arg or Lys; a $V_L$ CDR2 having the sequence KTN or NAN; and a $V_L$ CDR3 having the sequence X$_8$QYNSX$_9$PX$_{10}$T (SEQ ID NO: 34), wherein X$_8$ is Phe or Leu, X$_9$ is Gly or Trp, and X$_{10}$ is Arg or Leu (e.g., SEQ ID NO: 17 or SEQ ID NO: 23). In certain aspects, such an antibody is a humanized or de-immunized antibody comprising the foregoing CDRs on a human IgG (e.g., IgG1 or IgG2) backbone.

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody H225, which are represented by SEQ ID NOs: 12, 13, 14, 15, 16, and 17, respectively. In one aspect, the isolated antibody comprises CDR sequences that are identical to the CDR sequences of monoclonal antibody H225.

In another aspect, the isolated antibody comprises a $V_H$ domain at least about 80% identical to the $V_H$ domain of H225 (SEQ ID NO: 4) and a $V_L$ domain at least about 80% identical to the $V_L$ domain of H225 (SEQ ID NO: 5). In one aspect, the isolated antibody comprises $V_H$ and $V_L$ domains identical to those of monoclonal antibody H225.

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody Hj223.3, which are represented by SEQ ID NOs: 24, 13, 25, 15, 16, and 17, respectively. In one aspect, the isolated antibody comprises CDR sequences that are identical to the CDR sequences of monoclonal antibody Hj223.3.

In another aspect, the isolated antibody comprises a $V_H$ domain at least about 80% identical to the $V_H$ domain of Hj223.3 (SEQ ID NO: 8) and a $V_L$ domain at least about 80% identical to the $V_L$ domain of Hj223.3 (SEQ ID NO: 9). In one aspect, the isolated antibody comprises $V_H$ and $V_L$ domains identical to those of monoclonal antibody Hj223.3.

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody Hj20, which are represented by SEQ ID NOs: 18, 19, 20, 21, 22, and 23, respectively. In one aspect, the isolated antibody comprises CDR sequences that are identical to the CDR sequences of monoclonal antibody Hj20.

In another aspect, the isolated antibody comprises a $V_H$ domain at least about 80% identical to the $V_H$ domain of Hj20 (SEQ ID NO: 6 and a $V_L$ domain at least about 80% identical to the $V_L$ domain of Hj20 (SEQ ID NO: 7). In one aspect, the isolated antibody comprises $V_H$ and $V_L$ domains identical to those of monoclonal antibody Hj20.

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody Hj41.5, which are represented by SEQ ID NOs: 24, 26, 27, 28, 29, and 30, respectively. In one aspect, the isolated antibody comprises CDR sequences that are identical to the CDR sequences of monoclonal antibody Hj41.5.

In another aspect, the isolated antibody comprises a $V_H$ domain at least about 80% identical to the $V_H$ domain of Hj41.5 (SEQ ID NO: 10 and a $V_L$ domain at least about 80% identical to the $V_L$ domain of Hj41.5 (SEQ ID NO: 11). In one aspect, the isolated antibody comprises $V_H$ and $V_L$ domains identical to those of monoclonal antibody Hj20.

In some aspects, an antibody of the embodiments may be an IgG (e.g., IgG1, IgG2, IgG3 or IgG4), IgM, IgA, or an antigen binding fragment thereof. The antibody may be a Fab', a F(ab')2 a F(ab')3, a monovalent scFv, a bivalent scFv, or a single domain antibody. The antibody may be a human, humanized, or de-immunized antibody. In a further aspect, the isolated antibody is the H225, Hj223.3, Hj20 or Hj41.5 antibody.

In some aspects, the antibody may be conjugated to an imaging agent, a chemotherapeutic agent, a toxin, or a radionuclide.

In one embodiment, there is provided a recombinant polypeptide comprising an antibody $V_H$ domain comprising CDRs 1-3 of the $V_H$ domain of H225 (SEQ ID NOs: 12, 13 and 14); CDRs 1-3 of the $V_H$ domain of Hj223.3 (SEQ ID NOs: 24, 13 and 25); CDRs 1-3 of the $V_H$ domain of Hj20 (SEQ ID NOs: 18, 19 and 20); or CDRs 1-3 of the $V_H$ domain of Hj41.5 (SEQ ID NOs: 24, 26 and 27). In another embodiment, there is provided a recombinant polypeptide comprising an antibody $V_L$ domain comprising CDRs 1-3 of the $V_L$ domain of H225 (SEQ ID NOs: 15, 16 and 17); Hj223.3 (SEQ ID NOs: 15, 16 and 17); Hj20 (SEQ ID NOs: 21, 22 and 23); or Hj41.5 (SEQ ID NOs: 28, 29 and 30).

In some embodiments, there is provided an isolated polynucleotide molecule comprising nucleic acid sequence encoding an antibody or a polypeptide comprising an antibody $V_H$ or $V_L$ domain disclosed herein.

In further embodiments, a host cell is provided that produces a monoclonal antibody or recombinant polypeptide of the embodiments. In some aspects, the host cell is a mammalian cell, a yeast cell, a bacterial cell, a ciliate cell, or an insect cell. In certain aspects, the host cell is a hybridoma cell.

In still further embodiments, there is provided a method of manufacturing an antibody of the present invention comprising expressing one or more polynucleotide molecule(s) encoding a $V_L$ or $V_H$ chain of an antibody disclosed herein in a cell and purifying the antibody from the cell.

In additional embodiments, there are pharmaceutical compositions comprising an antibody or antibody fragment as discussed herein. Such a composition further comprises a pharmaceutically acceptable carrier and may or may not contain additional active ingredients.

In embodiments of the present invention, there is provided a method for treating a subject having a cancer comprising administering an effective amount of an antibody disclosed herein. In certain aspects, the antibody is a monoclonal antibody of the present invention, such as H225 or Hj223.3, or a recombinant polypeptide comprising antibody segment derived therefrom.

In certain aspects, the cancer may be a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In these aspects, the cancer is a JAM-C positive B-cell lymphoma.

In one aspect, the antibody may be administered systemically. In additional aspects, the antibody may be administered intravenously, intradermally, intratumorally, intramuscularly, intraperitoneally, subcutaneously, or locally. The method may further comprise administering at least a second anticancer therapy to the subject. Examples of the second anticancer therapy include, but are not limited to, surgical therapy, chemotherapy, radiation therapy, cryotherapy, hormonal therapy, immunotherapy, or cytokine therapy.

In further aspects, the method may further comprise administering a composition of the present invention more than one time to the subject, such as, for example, 1, 2, 3, 4, 5, 6, 7, 8, 9, 10, 15, 20 or more times.

In another embodiment, there is provided a method for detecting a cancer in a subject comprising testing for the presence of elevated JAM-C relative to a control in a sample from the subject, wherein the testing comprises contacting the sample with an antibody disclosed herein. For example, the method may be an in vitro or in vivo method.

Certain embodiments are directed to an antibody or recombinant polypeptide composition comprising an isolated and/or recombinant antibody or polypeptide that specifically binds JAM-C. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

In still further aspects, an antibody or polypeptide of the embodiments comprises one or more amino acid segments of the any of the amino acid sequences disclosed herein. For example, the antibody or polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 amino acids in length, including all values and ranges there between, that are at least 80, 85, 90, 95, 96, 97, 98, 99, or 100% identical to any of the amino acid sequences disclosed herein. In certain aspects the amino segment(s) are selected from one of the amino acid sequences of a JAM-C-binding antibody as provided in Table 1.

In still further aspects, an antibody or polypeptide of the embodiments comprises an amino acid segment of the any of the amino acid sequences disclosed herein, wherein the segment begins at amino acid position 1, 2, 3, 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in any sequence provided herein and ends at amino acid position 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in the same provided sequence. In certain aspects the amino segment(s), or portions thereof, are selected from one of the amino acid sequences of a JAM-C-binding antibody as provided in Table 1.

In yet further aspects, an antibody or polypeptide of the embodiments comprises an amino acid segment that is at least 80, 85, 90, 95, 96, 97, 98, 99, or 100% identical (or any range derivable therein) to a V, VJ, VDJ, D, DJ, J or CDR domain of a JAM-C-binding antibody (as provided in Table 1). For example, a polypeptide may comprise 1, 2 or 3 amino acid segment that are at least 80, 85, 90, 95, 96, 97, 98, 99, or 100% identical (or any range derivable therein) to CDRs 1, 2, and/or 3 a JAM-C-binding antibody as provided in Table 1.

In one embodiment, a composition comprising a JAM-C binding antibody is provided for use in the treatment of cancer in a patient. In another embodiment, the use of a JAM-C binding antibody in the manufacture of a medicament for the treatment of a JAM-C positive B-cell lymphoma is provided. Said JAM-C binding antibody may be any JAM-C binding antibody of the embodiments.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising," respectively.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-D: Human B cells (4-20×10$^6$), either incubated for 30 min with control IgG or with anti-JAM-C antibody, were injected into NOD/SCID mice. One hour after injection the mice were sacrificed and bone marrow (BM), spleen, lymph nodes (LNs) (mesenteric, inguinal, brachial, axillary, and cervical), and blood were analyzed by flow cytometry for the presence of human B cells, using anti-CD19 and anti-CD45 antibodies. Results of one representative experiment are shown. Gates indicate the number of human B cells recovered from BM (FIG. 1A), spleen (FIG. 1B), LNs (FIG. 1C), and blood (FIG. 1D), expressed as number of detected B cells per 10$^6$ cells acquired by flow cytometry per 10$^6$ B cells injected into the mice. FIGS. 1E-H: Effect of anti-JAM-C antibody on the homing of human B cells to BM (FIG. 1E), spleen (FIG. 1F), LNs (FIG. 1G), and blood (FIG. 1H) relative to control (control=100%). Data are expressed as mean±SD from seven independent experiments, two mice per experiment. Differences in homing between antibody-treated and control cells were analyzed using Student's t-test, $P<0.05$.

FIG. 4A: FACS analysis of B cells from blood of healthy donors, from patients with MZBL (JAM-Cpos), and from patients with CLL (JAM-Cneg), before injection into NOD/SCID mice. FIGS. 4B-C: LNs and BM (FIG. 4B), and spleen and peripheral blood (FIG. 4C) from NOD/SCID mice were obtained one hour after injection of human B cells, and analyzed by flow cytometry with anti-human CD19 and anti-human CD45 antibodies. Data indicate mean±SD of detected human B cells, per $10^6$ cells acquired by FACS, per $10^6$ injected B cells, either from healthy donors (black columns, n=8), from JAM-Cpos lymphoma patients (dark grey columns, n=5), or from JAM-Cneg lymphoma patients (light grey columns, n=3). Differences in homing between different groups were analyzed using ANOVA, followed by Tukey post-hoc analysis, $P<0.05$. FIGS. 4D-F: PBMCs from JAM-Cpos lymphoma patients treated with control IgG or with anti-human JAM-C antibody were injected into NOD/SCID mice and BM (FIG. 4D), spleen (FIG. 4E), and LNs (FIG. 4F) were analyzed as in (FIG. 4B). Columns show percentage of human B cells that homed to the organs relative to control (control=100%). Data are mean±SD from five independent experiments, two mice per experiment. Differences in the homing between antibody-treated and control cells were analyzed using Student's t-test, $P<0.05$.

FIG. 5A: Surface JAM-C expression was analyzed in Raji cells by flow cytometry using anti-JAM-C antibodies. Raji cells were transfected with the pcDNA plasmid encoding Neomycin resistance either without (pcDNAe) or with the full-length human JAM-C cDNA (HuJAM-C). FIG. 5B: Raji cells transfected with empty vector or with full-length human JAM-C were labeled with CFSE, incubated with rabbit IgG or with affinity-purified rabbit anti-JAM-C, and challenged for adhesion on coated soluble Fc-tagged molecules. Specific JAM-C related adhesion occurred only on wells coated with JAM-B. Pre-incubation of the cells with anti-human JAM-C antibody selectively inhibited the binding of JAM-C transfected cells to JAM-B and did not modify the binding to VCAM-1. The figure is representative of six independent experiments, three wells per condition. FIG. 5C: Raji cells, transfected with empty vector or with full-length human JAM-C, were labeled with CFSE and evaluated for adhesion on coated soluble Fc-tagged molecules. pcDNAe Raji cells did not adhere to any of the molecules tested, whereas HuJAM-C Raji cells adhered only to JAM-B. The figure is representative of six independent experiments, three wells per condition. FIG. 5D: Anti-human JAM-C rabbit polyclonal antibody inhibited the binding of Raji cells to JAM-B, but not to VCAM-1. Results show the percentage of cells incubated with rabbit anti-JAM-C related to the number of cells incubated with control rabbit IgG. Pre-incubation of cells with anti-human JAM-C selectively inhibited the binding of JAM-C transfected cells to JAM-B. Differences in the percentage of inhibition between cells transfected with empty vector or with full-length human JAM-C were analyzed using Student's t-test, $P<0.05$. FIG. 5E: Anti-JAM-C antibodies, but not anti-alpha-4 integrin antibodies, inhibited the binding of JAM-B Fc to JAM-Cpos Jeko-1 cells. JAM-B binding was calculated as the ratio of JAM-B Fc MFI and to Fc control MFI. No binding was observed with JAM-C negative cells (K1718). The figure is representative of three independent experiments.

FIG. 6A: Surface Plasmon Resonance analysis shows preferential JAM-B/JAM-C interaction. Sensograms of relative responses of soluble JAM-B Fc, JAM-B FLAG, and JAM-C Fc to immobilized JAM-C FLAG (the extracellular domain of the human soluble JAM-C FLAG protein was produced in BOSC cells and purified through an anti-FLAG affinity column) The background signal from a reference channel without soluble JAM-C was automatically subtracted. No association of JAM-C Fc to immobilized JAM-C was observed, whereas both JAM-B Fc and JAM-B FLAG associated with JAM-C. FIG. 6B: Surface Plasmon Resonance analysis. Relative response units (resonance units, RU) were recorded at the end of injection and subtracted from RU at the beginning of injection to check for the comparative association ability of murine and human JAM-B molecules to immobilized human JAM-C FLAG. No major differences were observed between human or murine JAM-B FLAG protein.

FIGS. 8A-C: Detection of normal human B cells in lymphoid organs of mice. FIG. 8A: Quantification of human B cells in NOD/SCID mice. Human B cells from healthy donors (between 4 and $20\times10^6$, depending on the number of B cells recovered after the enrichment procedure) were injected into NOD/SCID mice. One hour after injection the mice were sacrificed and BM, spleen, and LN were analyzed by FACS for the presence of B cells using human-specific anti-CD19 and anti-CD45 antibodies. The number of B cells was quantified as the number of CD45pos-CD19pos cells per $10^6$ total acquired cells by FACS, per $10^6$ injected B cells. The results show that in experiments with 4 and $20\times10^6$ injected B cells, respectively, the normalized number of recovered B cells was almost identical in BM, spleen, and LN. FIG. 8B: Detection of human B cells incubated with rabbit anti-human CD19. Pre-incubation of human cells with rabbit anti-CD19 did not compete with subsequent recognition of B cells by mouse anti-human CD19, since staining with anti-CD20 or anti-CD19 resulted in recognition of identical human B cell populations. FIG. 8C: Rabbit anti-human CD19 antibody does not influence homing Human B cells (4-20×10$^6$) treated with control IgG or with rabbit anti-CD19 antibody were injected into NOD/SCID mice. Blood, BM, spleen, and LN were analyzed as described in FIG. 8A. Columns show the percentage of human B cells that homed to the different organs relative to control cells (control=100%). Data are mean±SEM from three independent experiments.

FIGS. 9A-C: Analysis of human B cell migration to lymphoid organs of NOD/SCID mice. Human B cells were injected into NOD/SCID mice. One hour after injection mice were sacrificed and lymphoid organs were collected. Panels show BM (FIG. 9A), spleen (FIG. 9B), and LN (FIG. 9C) sections stained with anti-human CD79 antibody. The number of human B cells counted in one microscopic field is indicated in each panel (one representative field). Left panels: control mice injected with IgG-treated B cells; right panels: mice injected with anti-JAM-C-treated B cells.

FIGS. 12A-B: Distribution of JAM-C negative B cells treated with anti-JAM-C antibody as a control. FIG. 12A: Analysis of the homing pattern of JAM-Cneg cells treated with anti-JAM-C antibodies. JAM-Cneg human B cells (4-20×10$^6$), either incubated for 30 min with control IgG or with anti-JAM-C antibody, were injected into NOD/SCID mice. One hour after injection the mice were sacrificed and organs were analyzed. The number of B cells was quantified as the number of CD45pos-CD19pos cells per 10$^6$ total acquired cells by FACS, per 10$^6$ injected B cells. Effect of anti-JAM-C antibody on the number of human B cells in blood, BM, spleen, and LNs, compared to control (control=100%). Data are mean±SEM from two independent experiments, two mice per experiment. FIG. 12B: Analysis of liver in short-term assays. Human B cells (4-20×10$^6$) incubated for 30 min either with control IgG or with anti-JAM-C antibody were injected into NOD/SCID mice. One hour after injection the mice were sacrificed and liver was collected and analyzed for the presence of human B cells. Effect of anti-JAM-C antibody on the percentage of human B cells recovered from the liver, compared to control (control=100%). Data are mean±SD from seven independent experiments, two mice per experiment. Differences in homing between antibody treated and control cells were analyzed using Student's t-test, P<0.05.

FIGS. 13A-C: JAM-B Fc binds to JAM-Cpos cells, independently of alpha-4 integrin. FIG. 13A: Adhesion experiments of JAM-Cpos cell lines on immobilized soluble JAM-B protein. Jeko-1 (JAM-Cpos) and K1718 (JAM-Cneg) cells were seeded on microplate culture wells coated with either JAM-B Fc or with control Fc protein. Data are expressed as the ratio of the fluorescence of JAM-B Fc coated wells to the fluorescence of Fc protein coated control wells. Mean of three independent experiments. FIG. 13B: B and non-B cell lines were analyzed for their capacity to bind soluble JAM-B. Cells were incubated with either recombinant human IgG1 Fc as control or with soluble human JAM-B Fc. JAM-B Fc binding was calculated as the ratio of JAM-B Fc MFI to Fc control MFI, and expressed as a function of JAM-C expression (the ratio of anti-JAM-C MFI to isotype control IgG MFI). Raji pcDNA (mock-transfected Raji cells) and K1718 do not express JAM-C; Raji HuJAM-C X, Raji HuJAM-C Y (two different batches of JAM-C transfected Raji cells), Jeko-1, HUVEC, and transfected MDCK, CHO and K562 are JAM-Cpos cells. FIG. 13C: Binding experiments of JAM-B Fc to cell lines expressing alpha-4 integrin ±JAM-C. Soluble JAM-B bound only to JAM-Cpos cells. Although all cells express alpha-4 integrin, pre-incubation with anti-alpha-4 integrin antibody did not influence JAM-B binding.

FIG. 19A: JAM-Cpos lymphomas were cultured with CD40L and cytokines and treated with either control IgG or JAM-C mAb (10 mg/mL). Proliferation was quantified using Draq5 and EdU FACS analysis. FIG. 19B: Normal B cells were incubated with JAM-C mAb in suspension for 72 h. FIG. 19C: Normal B cells were incubated with bead-bound anti-JAM-C mAb for 5 and 24 h. FIG. 19D: JAM-Cpos lymphoma cells were incubated with JAM-C mAb in suspension for 72 h.

FIG. 20A: Jeko-1 cells were incubated with anti-JAM-C mAb for 30 min and 3 h, and analyzed for phospho-ERK1/2 levels. N=5. FIG. 20B: Primary B cells were activated with CD40L and cytokines, incubated with anti-JAM-C mAb for 30 min and 3 h, and analyzed for phospho-ERK1/2 levels. FIG. 20C: Primary JAM-Cpos lymphoma B cells were isolated from four patient samples of mantel cell lymphoma, activated with CD40L and cytokines, and incubated with anti-JAM-C mAb for 30 minutes, and analyzed for phospho-ERK1/2 levels. One representative experiment is shown.

DESCRIPTION OF ILLUSTRATIVE EMBODIMENTS

I. The Present Invention

Figure 1:
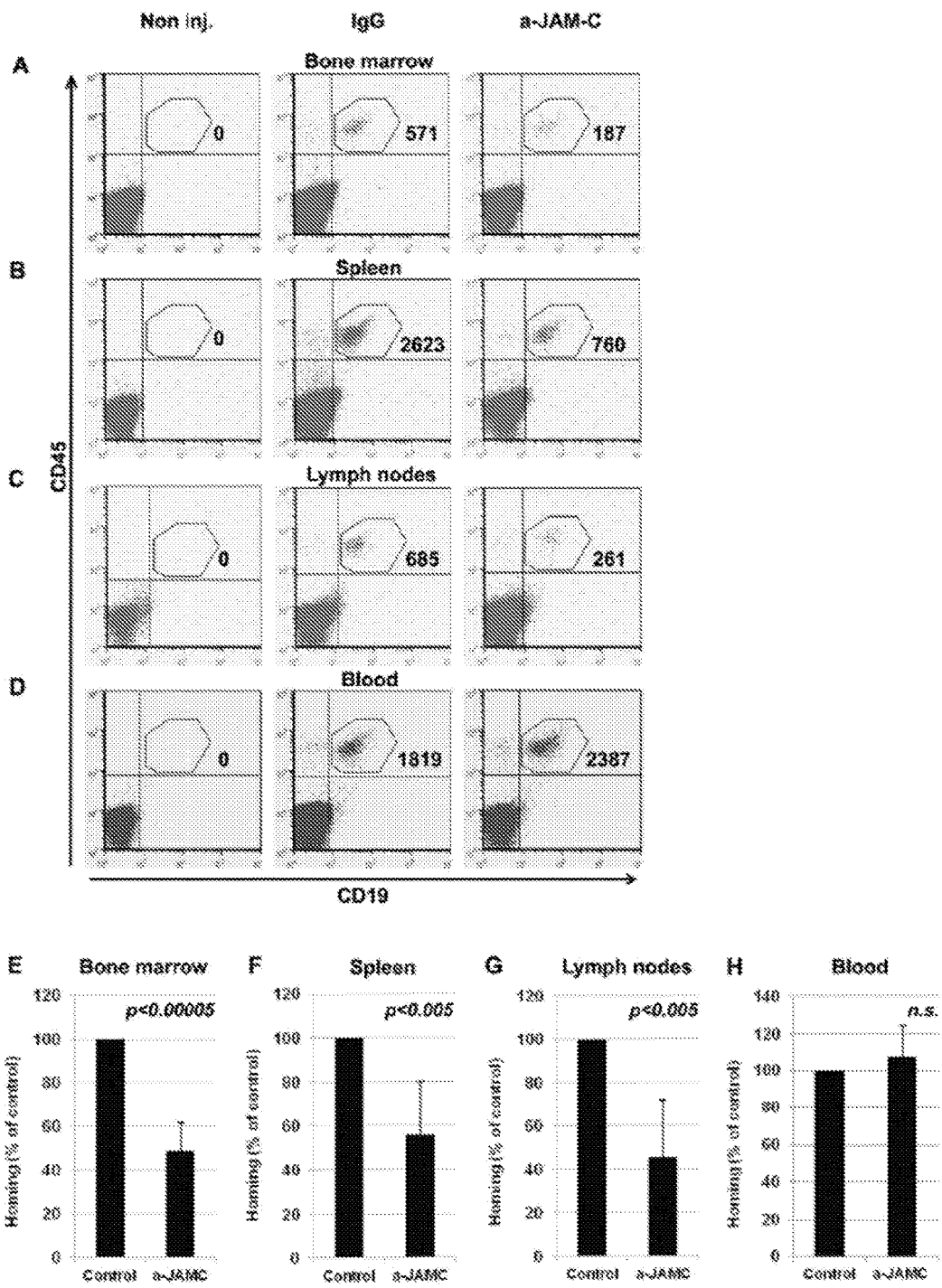
FIGS. 1A-H: Homing of normal human B cells to lymphoid organs is reduced by anti-JAM-C antibodies.

The present invention is based, in part, on the finding that B-cell lymphoma engraftment is controlled by JAM-C. As such, anti-JAM-C antibodies block adhesion of JAM-C-expressing B cells to their ligand, JAM-B, which is expressed on, for example, human and murine lymphatic endothelial cells. The inventors used adoptive transfer of human B cells into immune deficient NOD/SCID mice to perform short-term homing assays. This model is widely used for the study of human B cell migration in vivo, since the major endothelial integrin ligands, chemokines, selectins, and selectin ligands of lymphoid organs are highly conserved between human and mouse (Hartmann et al., 2009; Lapidot and Kollet, 2002; Mosier et al., 1988). Studies detailed here, for example, show that treatment with anti-JAM-C antibodies in short-term experiments reduced migration of normal and malignant JAM-C expressing B cells to bone marrow, lymph nodes, and spleen of mice. Furthermore, long-term administration of anti-JAM-C antibodies prevented engraftment of JAM-Cpos lymphoma cells in bone marrow, lymph nodes, and spleen of mice. Aspects of the present embodiments can be used to prevent lymphoma cells, e.g., JAM-Cpos B-cell lymphoma cells, from reaching supportive microenvironments, including the spleen, where malignant cells survive and proliferate thus contributing to disease progression. In particular, certain embodiments concern polypeptides (e.g., polypeptides comprising antibody CDR domains) that specifically bind to JAM-C and block homing to and engraftment of JAM-Cpos lymphoma cells in the bone marrow, lymph nodes, and spleen.

II. JAM-C

Junctional adhesion molecule C (JAM-C) belongs to the Ig superfamily and is composed of two extracellular Ig-like domains and a cytoplasmic tail with a PDZ binding motif (Weber et al., 2007). JAM-C has been described as an endothelial adhesion molecule localized at tight junctions and expressed by high endothelial venules and lymphatic vessels in lymphoid organs. JAM-C expression has also been described on human hematopoietic cells, e.g., platelets, some activated T cells, and NK cells (Bradfield et al., 2007), and JAM-C is expressed on the surface of normal and malignant B cells. Its differential expression defines B cell differentiation stages and distinguishes memory germinal center B cells (CD27pos, JAM-Cneg) from memory non-GC B cells (CD27pos, JAM-Cpos) (Ody et al., 2007). The expression of JAM-C in different B-cell lymphomas allows the classification of two types of B-cell malignancies: JAM-Cneg (e.g., chronic lymphocytic leukemia (CLL), follicular lymphoma (FL), diffuse large B lymphoma (DLBL)) and JAM-Cpos (e.g., marginal zone B-cell lymphoma (MZBL), hairy cell leukemia (HCL)) lymphomas.

JAM-C is an adhesion molecule localized at endothelial tight junctions. In humans, it is also present on platelets, dendritic cells, and subsets of T, NK, and B cells (Bradfield et al., 2007). While the function of JAM-C at vascular tight junctions has been described (Orlova et al., 2006; Sacharidou et al., 2010; Li et al., 2009), little is known about the role of JAM-C on circulating hematopoietic cells. Only a few reports have suggested that the interaction of JAM-C on human lymphocytes with endothelial JAM-B might be involved in trafficking of these cells through endothelial barriers (Arrate et al., 2001; Liang et al., 2002). In vivo experiments with B cells are further complicated by the fact that only human, but not murine, B cells express JAM-C.

Several interactions for JAM-C have been described, including homophilic JAM-C/JAM-C, heterophilic JAM-C/MAC-1 (alphaM-beta2), and heterophilic JAM-C/JAM-B interactions (Weber et al., 2007). Among these, JAM-B, expressed by endothelial cells, seems to be the major ligand for JAM-C (Arrate et al., 2001; Liang et al., 2002). Thus, JAM-C on human leukocytes could interact with vascular JAM-B to mediate leukocyte adhesion and transmigration.

III. Therapeutic Antibodies

In certain embodiments, an antibody or a fragment thereof that binds to at least a portion of JAM-C protein and inhibits JAM-C-mediated colonization of lymphoid tissues by B cells and its associated use in treatment of diseases are contemplated. As used herein, the term "antibody" is intended to refer broadly to any immunologic binding agent, such as IgG, IgM, IgA, IgD, and IgE as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-JAM-C antibody is a monoclonal antibody or a humanized antibody. By known means and as described herein, polyclonal or monoclonal antibodies, antibody fragments, and binding domains and CDRs (including engineered forms of any of the foregoing) may be created that are specific to JAM-C protein, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

JAM-C mRNA sequences (SEQ ID NO: 1) may be used to produce recombinant proteins and peptides as well known to people skilled in the art. For example, such mRNA sequences could be engineered into a suitable expression system, e.g., yeast, insect cells, or mammalian cells, for production of a JAM-C protein or peptide. For example, expression systems may be used to produce a soluble JAM-C polypeptide provided here in SEQ ID NO: 2.

Animals may be inoculated with an antigen, such as a FLAG-tagged soluble JAM-C protein (see SEQ ID NO: 2), in order to produce antibodies specific for JAM-C protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a JAM-C antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881, 557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939, 350; 3,996,345; 4,196,265; 4,275,149; 4,277,437; 4,366, 241; 4,469,797; 4,472,509; 4,606,855; 4,703,003; 4,742, 159; 4,767,720; 4,816,567; 4,867,973; 4,938,948; 4,946, 778; 5,021,236; 5,164,296; 5,196,066; 5,223,409; 5,403, 484; 5,420,253; 5,565,332; 5,571,698; 5,627,052; 5,656, 434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946, 546, which is incorporated herein by reference. These techniques are further described in: Marks (1992); Stemmer (1994); Gram et al. (1992); Barbas et al. (1994); and Schier et al. (1996).

It is fully expected that antibodies to JAM-C will have the ability to neutralize or counteract the effects of JAM-C regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds JAM-C.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against JAM-C, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6?-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

IV. Treatment of Diseases

Certain aspects of the present embodiments can be used to prevent or treat a disease or disorder associated with JAM-C-mediated B-cell homing to lymphoid tissues. Functioning of JAM-C may be reduced by any suitable drugs to prevent B-cell colonization of lymphoid tissues. Preferably, such substances would be an anti-JAM-C antibody.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits the JAM-C-mediated colonization of lymphoid tissues by cancerous B cells.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A. Pharmaceutical Preparations

Where clinical application of a therapeutic composition containing an inhibitory antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

B. Combination Treatments

In certain embodiments, the compositions and methods of the present embodiments involve an antibody or an antibody fragment against JAM-C to inhibit its activity in colonization of lymphoid tissues by B cells, in combination with a second or additional therapy. Such therapy can be applied in the treatment of any disease that is associated with JAM-C-mediated colonization of lymphoid tissues by B cells. For example, the disease may be B-cell lymphoma.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

i. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

ii. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

iii. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

iv. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

V. Kits and Diagnostics

In various aspects of the embodiments, a kit is envisioned containing therapeutic agents and/or other therapeutic and delivery agents. In some embodiments, the present embodiments contemplates a kit for preparing and/or administering a therapy of the embodiments. The kit may comprise one or more sealed vials containing any of the pharmaceutical compositions of the present embodiments. The kit may include, for example, at least one JAM-C antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Blocking of Normal Human B Cell Homing to Lymphoid Organs by Anti-JAM-C Antibody Human B cells from peripheral blood of healthy donors were incubated with affinity-purified rabbit anti-JAM-C antibody or control IgG and injected into the tail veins of NOD/SCID mice. One hour post-injection, B cells were quantified in BM, spleen, LNs, and blood by flow cytometry using human-specific anti-CD45 and anti-CD19 antibodies (FIG. 1A-D). Affinity-purified rabbit anti-JAM-C antibody specifically decreased the homing of B cells to BM, spleen, and LNs, but did not alter the number of B cells in circulation (FIG. 1). The same results were obtained by treatment of B cells with affinity-purified goat anti-JAM-C antibody. Pre-incubation of B cells with rabbit anti-human CD19 antibody did not influence the homing (FIG. 8C), demonstrating the specific effect of anti-JAM-C antibody.

For B cell homing assays, human B cells obtained from healthy donors or from patients with a leukemic B-cell lymphoma were injected into the tail vein of non-irradiated 4-8 week-old NOD/SCID mice (4-20×10$^6$ cells per mouse). For blocking experiments, B cells were incubated 30 min prior to injection with rabbit—(Ody et al., 2007) or goat—(R&D) anti-JAM-C affinity-purified antibodies (10 µg/mL), with anti-alpha-4 integrin antibody (0.5 µg/mL, clone HP2/1, AbD Serotec), or a combination of both. Polyclonal anti-JAM-C antibodies were used to ensure maximal blocking of epitopes on the JAM-C antigen. In control experiments, B cells were incubated with the same concentration of either rabbit IgG, goat IgG, a combination of rabbit and mouse IgG, or rabbit anti-human CD19 (Abgent), as an irrelevant binding antibody. One hour after injection, mice were sacrificed and blood, liver, BM, spleen, and LNs (mesenteric, inguinal, brachial, axillary, and cervical) were collected. Human B cells from the different organs were detected by flow cytometry using human-specific anti-CD45 and anti-CD19 antibodies and quantified by normalizing the number of B cells detected in 10$^6$ cells acquired by FACS, per 10$^6$ of injected B cells. Non-injected mice were used as controls.

Human samples were obtained after informed consent and used according to the procedures approved by the local ethics committee and the Declaration of Helsinki. Peripheral blood was obtained from healthy blood donors and from patients with leukemic B-cell lymphomas. Mononuclear cells were collected following standard separation on Ficoll-Paque (GE-Healthcare). B cells were enriched by negative selection using a human B cell enrichment kit (EasySep, StemCell technologies), according to manufacturer's instructions.

NOD.CB17-Prkdcscid/J (NOD/SCID) mice were bred under defined flora conditions at the University Medical Center, University of Geneva, in sterile micro isolator cages. All experiments were approved by the Animal Care Committee of Geneva and by the Swiss National Veterinary Law.

For statistical analysis, Statistica 7.0 software was used. The significance of differences between groups was determined using Student's t-test or ANOVA followed by Tukey post hoc analysis. Results are expressed as mean±SD (standard deviation), with $P<0.05$ considered significant.

To study the localization of migrated human B cells in lymphoid organs, tissue sections were stained with the B-cell marker anti-CD79. In accordance to the results obtained from flow cytometry, a reduced number of B cells were observed in the tissue sections when cells were incubated with anti-JAM-C antibodies (FIG. 9).

For histological staining, paraffin-embedded BM, spleen, and LN sections were obtained from mice one hour after cell injection. H&E staining was performed according to standard procedures Immunohistochemistry was performed using mouse monoclonal biotinylated antibodies against CD79α (clone JCB117, Dako) at a dilution of 1:50. Antigen retrieval was performed with 10 min in a microwave oven at 98° C. in a 10 mM citrate buffer pH 6. Visualization was accomplished by horse-radish peroxidase with Dako Envison (Dako). At the end of the procedure, cell nuclei were counterstained with hematoxylin for 5 min. Images were visualized under light microscopy with an Axioskop 40 (Carl Zeiss) and captured with a Nikon D70 digital camera (Nikon).

Figure 10:
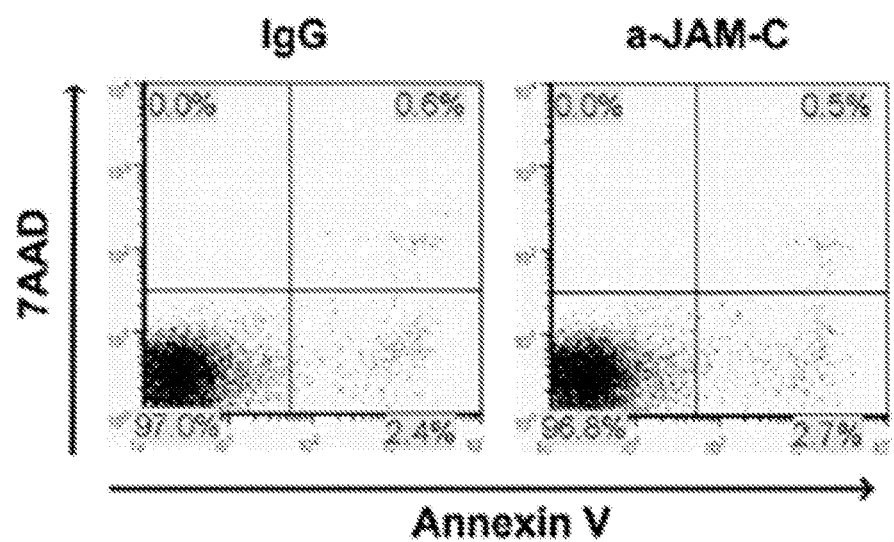
FIG. 10: Effects of anti-JAM-C antibody binding on apoptosis of human B cells. Cell viability and apoptosis measured by 7AAD/Annexin V staining Human B cells were cultured for one hour in the presence of control IgG or anti-JAM-C antibody. Cells were analyzed by flow cytometry using 7AAD and Annexin V staining.
Figure 11:
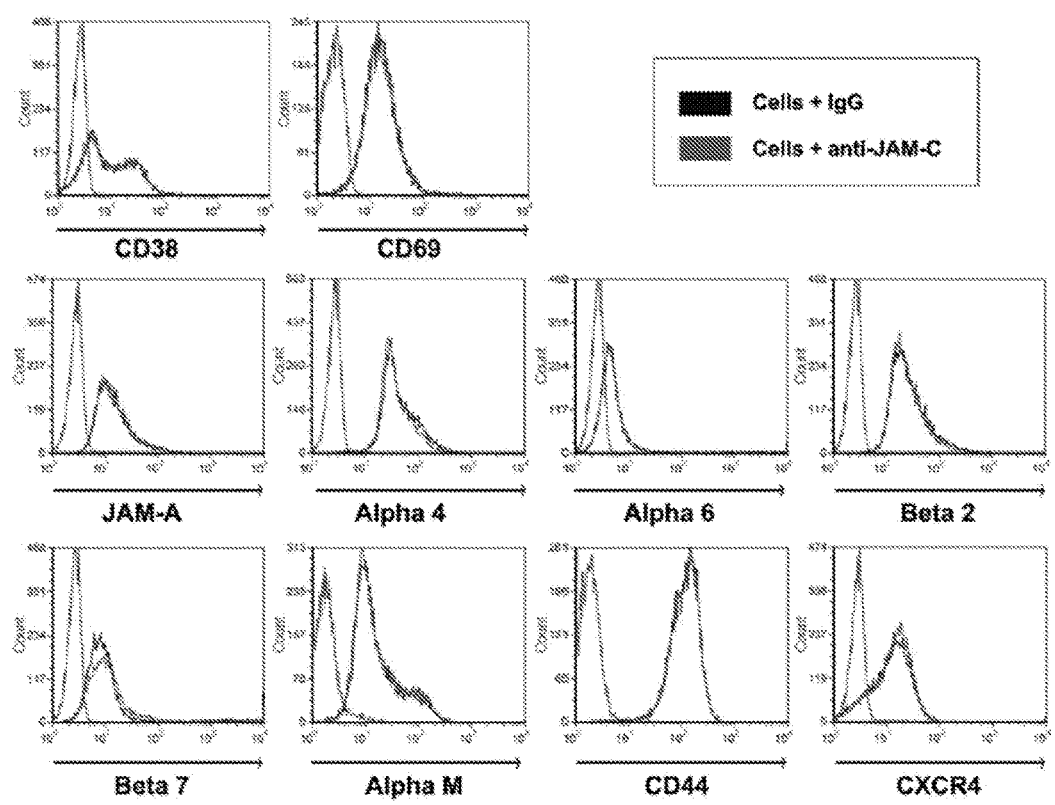
FIG. 11: Incubation of B cells with anti-JAM-C antibodies does not affect expression of activation markers or adhesion molecules. Human B cells were treated with control IgG or with affinity-purified anti-JAM-C antibody for 30 min and expression of cell surface activation markers and adhesion molecules were assessed by flow cytometry. Unstained cells were used as controls. One representative experiment out of three is shown.

To exclude any possible effects of anti-JAM-C antibody binding on B cell viability, cells were cultured for one hour in the absence or presence of antibody. No differences in the percentages of apoptotic or dead cells were detected between anti-JAM-C-treated and control cells (FIG. 10). To further exclude any indirect effects of antibody treatment, expression of activation markers CD69 and CD38, chemokine receptor CXCR4, adhesion molecules CD44, JAM-A, and the integrin subunits alpha-M, alpha-6, beta-2, alpha-4, and beta-7 were compared on anti-JAM-C-treated and control B cells. No significant differences in expression were observed for any of the markers examined (FIG. 11). To demonstrate the specificity of anti-JAM-C antibody, additional experiments were performed using JAM-Cneg B cells. Anti-JAM-C treatment did not alter the homing pattern of these cells (FIG. 12A).

To assess cell surface expression, flow cytometry was used as previously described (13). The following antibodies were used: directly conjugated anti-alphaM-PC5 and anti-CD38-PC5 (Beckman Coulter), anti-CD69-PC7 (BD Pharmingen), anti-CD44-FITC (BD Bioscience), anti-CXCR4-PE (R&D Systems), non-conjugated anti-JAM-A (kind gift of H. Ozaki (Zen et al., 2005)), and the integrins anti-alpha-6 (Ruiz et al., 1993), anti-beta-2 (TS1/18, Biolegend), anti-alpha-4 (AbD Serotec), and anti-beta-7 (BD Biosciences). Cells were incubated for 20 min at RT, washed, and when necessary, incubated with secondary antibody for an additional 20 min followed by another round of washing. Data were acquired by flow cytometry using a FC-500 flow cytometer (Beckman&Coulter) and analyzed using FCS express software (De Novo Software). Cell viability and apoptosis were measured by 7AAD/Annexin 5 staining (BD Pharmingen) following the manufacturer's instructions.

To investigate the localization of the cells when the homing to the lymphoid organs was blocked, B cells were pre-incubated with anti-JAM-C antibody and quantified in the liver one hour post-injection. As shown in FIG. 12B, cells treated with anti-JAM-C antibody partially redistributed to the liver.

Figure 2:
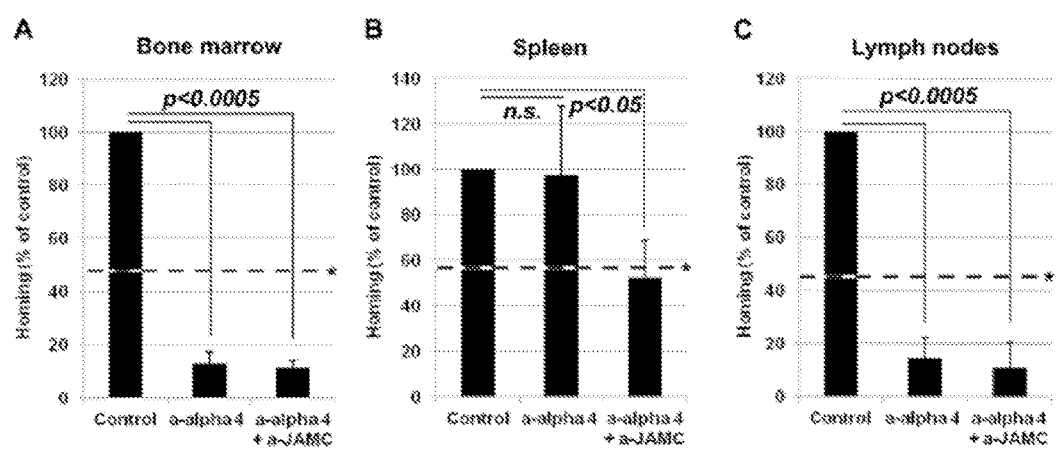
FIGS. 2A-C: Homing of normal human B cells is inhibited by a combination of anti-JAM-C and anti-alpha-4 integrin antibodies. Human B cells (4-20×10$^6$), treated for 30 min with control IgG, with anti-alpha-4 integrin antibody, or with a combination of anti-alpha-4 integrin and anti- JAM-C antibodies were injected into NOD/SCID mice. One hour after injection the mice were sacrificed and BM, spleen, and LNs were analyzed by flow cytometry for the presence of human B cells, using anti-CD19 and anti-CD45 antibodies. Data show percentage of human B cells that homed to BM (FIG. 2A), spleen (FIG. 2B), and LNs (FIG. 2C) relative to control (control=100%). Data correspond to mean±SD of four independent experiments, three mice per experiment. Differences in homing between antibody treated and control cells were analyzed using ANOVA, followed by Tukey post-hoc analysis, $P<0.05$.

Since alpha-4 integrin (VLA-4) is an important adhesion molecule implicated in B cell homing (Hartmann et al., 2009; Luster et al., 2005), the inventors compared the effects of anti-JAM-C antibody treatment to treatment with anti-alpha-4 integrin antibody or treatment with a combination of anti-JAM-C and anti-alpha-4 integrin antibodies on B cell homing Alpha-4 integrin antibody decreased homing to BM and LNs to a greater extent than anti-JAM-C alone but had no effect on homing to the spleen. The combination of both antibodies resulted in inhibition of homing to all three lymphoid organs (FIG. 2).

Example 2—Expression of JAM-C by Human B-Cell Lymphomas

Figure 3:
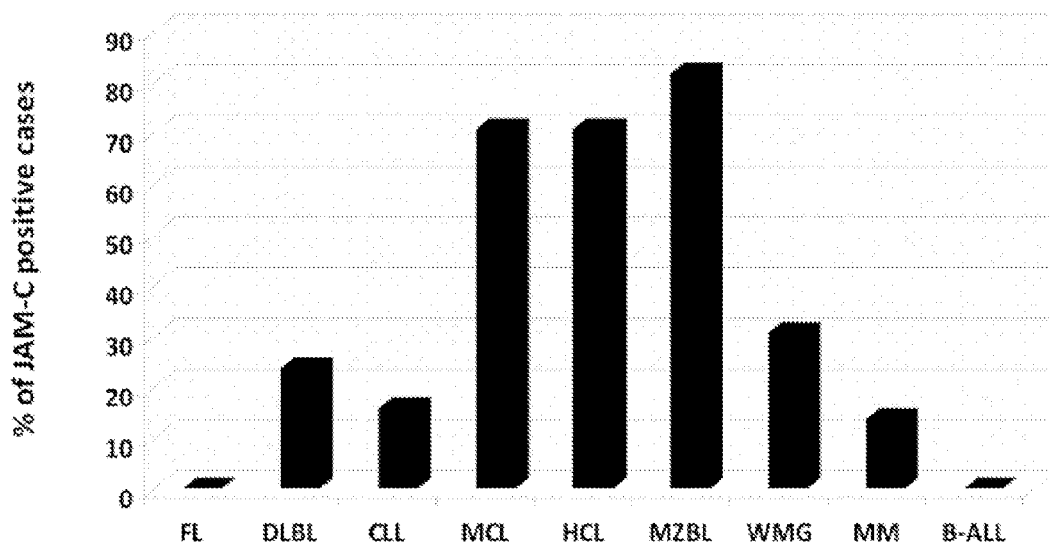
FIG. 3: JAM-C expression by human B-cell lymphomas. Different types of human B-cell lymphomas were studied by flow cytometry for the expression of JAM-C: 8 FL (follicular lymphoma), 17 DLBL (diffuse large B-cell lymphoma), 44 CLL (chronic lymphocytic leukemia), 21 MCL (mantle cell lymphoma), 7 HCL (hairy cell leukemia), 38 MZBL (marginal zone B-cell lymphoma), 16 WM (Waldenstroem's macroglobulinemia), 7 MM (multiple myeloma), and 5 ALL-B (acute lymphoblastic leukemia) cases. Cases were considered JAM-C positive if >20% of cells stained positive.

The inventors analyzed 163 human B-cell lymphomas for JAM-C expression (FIG. 3). The expression of JAM-C in B-cell lymphomas revealed a disease-specific pattern distinguishing JAM-Cpos from JAM-Cneg B-cell lymphomas. Therefore, JAM-C expression clearly allows the distinction between JAM-Cpos lymphomas (MZBL, MCL, HCL) and JAM-Cneg lymphomas (CLL, FL).

To determine JAM-C expression, cell samples were incubated with JAM-C rabbit antiserum at a dilution of 1:2000 after incubation with normal human serum. Reactivity was revealed with a human absorbed goat anti-rabbit IgG-PE or IgG-Alexa (Southern Biotechnology, Birmingham, Ala.). Preimmune serum of the same rabbit at the same dilution was used as a control. Samples were obtained using a FC-500 flow cytometer (BD) and analyzed using FCS express software.

Figure 4:
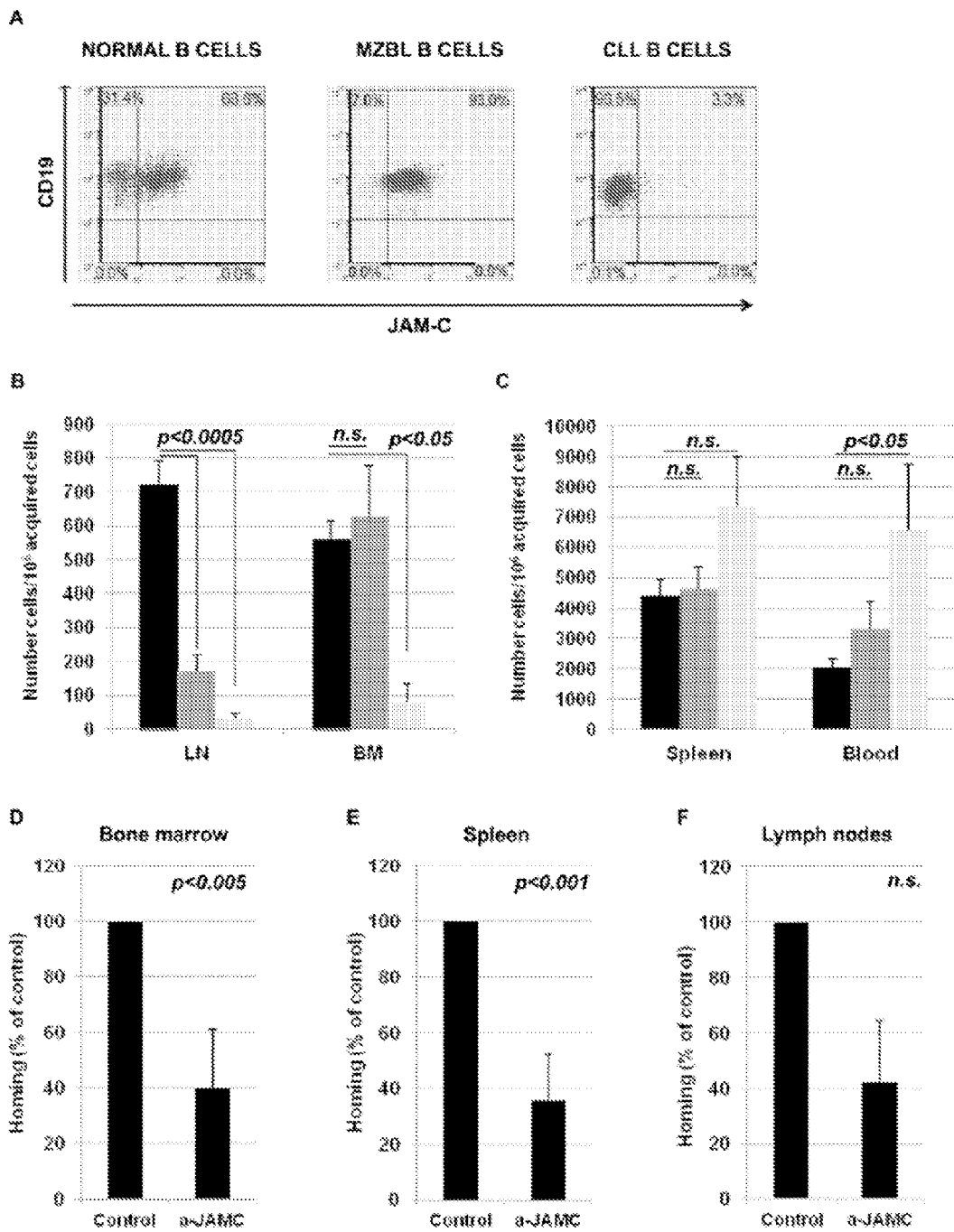
FIGS. 4A-F: JAM-Cpos lymphoma B cells show a specific homing pattern to lymphoid organs, which can be influenced by anti-JAM-C antibodies.

Example 3—Blocking of Malignant Lymphoma B Cell Homing to Lymphoid Organs by Anti-JAM-C Antibodies Since JAM-C is involved in normal B lymphocyte homing, the inventors investigated whether migration of malignant lymphoma B cells to lymphoid organs could also be impaired by anti-JAM-C antibodies. B cells from patients with JAM-Cpos or JAM-Cneg lymphomas, as well as from healthy donors, were injected into NOD/SCID mice (FIG. 4A). Blood, BM, spleen, and LNs were analyzed one hour after injection. The homing of JAM-Cpos lymphoma B cells to LNs was reduced by 77% compared to normal B lymphocytes, while no difference in migration to BM or spleen was observed (FIG. 4B-C). JAM-Cneg CLL B cells failed to reach LNs and BM of NOD/SCID mice, but were found primarily in blood and spleen (FIG. 4B-C). Similarly to normal B lymphocytes, the homing of JAM-Cpos lymphoma B cells to BM, spleen, and LNs was substantially decreased by anti-JAM-C antibody (FIG. 4D-F).

Figure 5:
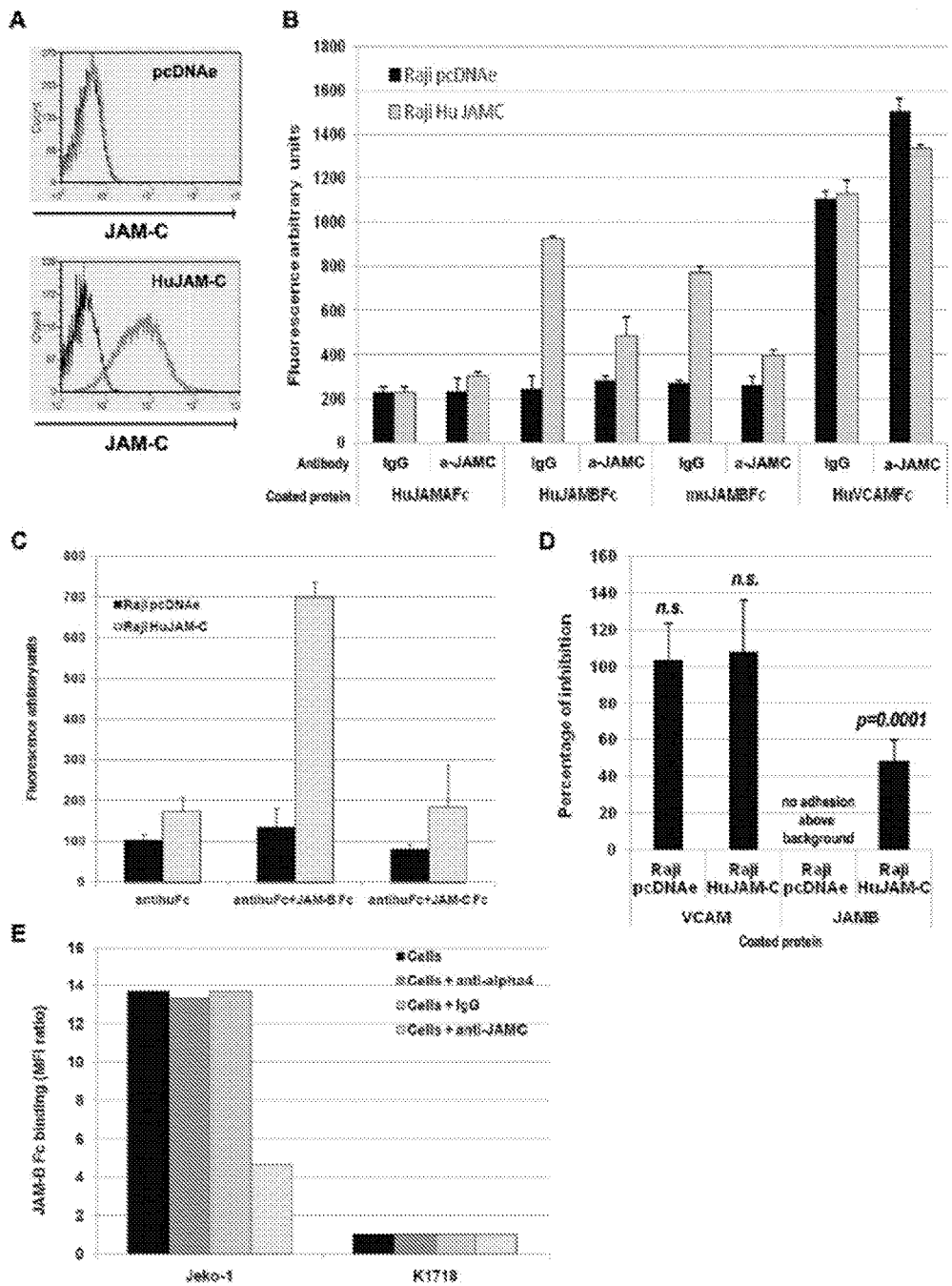
FIGS. 5A-E: Human JAM-C interacts with JAM-B, but not with JAM-C.

Example 4—Selective Blocking of Adhesion of JAM-C Positive B Cells to Mouse and Human JAM-B by Anti-JAM-C Antibodies To determine the mechanism leading to the reduction of B cell homing after anti-JAM-C treatment, the inventors identified the molecular ligands of JAM-C on B cells. Although homotypic JAM-C/JAM-C and heterotypic JAM-C/JAM-B interactions have been reported, the endothelial ligand for JAM-C on B cells had not been described. To investigate this interaction, adhesion assays were performed. Culture plates were coated with recombinant human and murine JAM-B Fc, human JAM-C Fc, human VCAM-1 Fc as a positive control, and JAM-A Fc as a negative control. The JAM-Cneg B cell line Raji was transfected with the full-length human JAM-C cDNA and mock-transfected cells were used as a control (FIG. 5A). Whereas mock-transfected Raji cells adhered only to VCAM-1, JAM-C transfected Raji cells adhered to JAM-B and VCAM-1, but adhered neither to JAM-C nor to JAM-A (FIG. 5B-C). Binding to VCAM-1 occurred through alpha-4 integrin, as it was abrogated by incubation of cells with anti-alpha-4 integrin antibody. Incubation of JAM-Cpos Raji cells with anti-human JAM-C antibody selectively inhibited the binding of Raji cells to murine and human JAM-B without affecting the binding to VCAM-1 (FIG. 5B,D). In parallel experiments with K1718

(JAM-Cneg) and Jeko-1 (JAM-Cpos) B cell lines, only Jeko-1 cells adhered to immobilized JAM-B Fc (FIG. 13A).

The human cell lines Jeko-1 (MCL) and K1718 (MZBL) were a kind gift from J. A. Martinez-Climent (Laboratory of Molecular Oncology, Center for Applied Medical Research, University of Navarra, Spain). The cell lines Raji, MDCK, CHO, K562 and were purchased from the American Type Culture Collection (ATCC). The cell line HUVEC was produced in the inventor's laboratory. Cell line phenotypes were tested and authenticated by flow cytometry before use.

For cell adhesion assays, NUNC 269787 adhesion plates were successively coated with anti-huFc antibody (Jackson Immuno Research) at 2.5 µg/mL, Fc-labeled proteins at 2.5 µg/mL, and blocked with 1% BSA (purified fraction V, Sigma). Cells were labeled with CFSE as recommended by the manufacturer (Invitrogen) and Fc-receptors were blocked (Fc-blocking solution; Miltenyi Biotech). The cells were then incubated in DMEM without Phenol red in the presence of rabbit IgG or anti-human JAM-C affinity-purified polyclonal antibody for 15 minutes at RT. Finally, $10^5$ to $5 \times 10^5$ cells were added per well and incubated for 30 minutes in a $CO_2$ incubator at 37° C. At the end of this incubation, the wells were carefully washed with PBS before adding 150 µL of 1% SDS in PBS for at least 4 hours with agitation at RT. One hundred microliters of lysed cells were transferred into a 96-well plate (micro-clear plates black, Greiner), and fluorescence ($\pi$ex 485 nm; $\pi$em 538 nm) was measured with a Flex Station Microplate reader (Molecular Devices). Data were expressed either in arbitrary units or as the ratio of the fluorescence measured on JAM-B Fc coated wells to the fluorescence measured on wells coated with Fc control protein.

To further illustrate the interaction of JAM-B as a ligand for JAM-C, binding assays of soluble JAM-B Fc were performed with various B and non-B cell lines, expressing different levels of JAM-C. A clear correlation between the level of expression of JAM-C and the binding of JAM-B was found (FIG. 13B).

For soluble protein binding assays, different cell types expressing different levels of JAM-C were used, including: Raji pcDNA (mock-transfected control) and K1718 as JAM-Cneg cells; Raji HuJAM-C X, Raji HuJAM-C Y (two different batches of JAM-C transfected Raji cells), Jeko-1, HUVEC, transfected MDCK, CHO, and K562 as JAM-Cpos cells. Cells ($2 \times 10^5$ cells per well) were incubated with either recombinant human IgG1 Fc (R&D) as a control or human JAM-B Fc (R&D) at 1 ug/mL for 60 min at 4° C. in PBS-BSA. In blocking experiments, cells were pre-incubated with anti-alpha-4 integrin antibody (1 µg/mL, clone HP2/1, AbD Serotec) or affinity-purified anti-human JAM-C polyclonal antibody. After washing, cells were incubated for 60 min at 4° C. with DyLight 488 goat anti-human IgG1Fc fragment (F(ab), Affinity purified (Jackson lab)) and analyzed on a FACScalibur (BD). Mean fluorescence values were calculated using Cellquest software and the data expressed as the ratio of JAM-B Fc MFI to Fc control MFI.

JAM-B is known to interact with α4β1 integrin expressed by T cells, and this interaction occurs only on cells that concomitantly express JAM-C (Cunningham et al., 2002). To investigate whether this mechanism could be involved in B cells, Jeko-1 and K1718 cells (both alpha-4 integrin positive) were incubated with anti-JAM-C or anti-alpha-4 integrin antibodies, and binding of soluble JAM-B Fc was analyzed by flow cytometry. JAM-B Fc bound to JAM-Cpos Jeko-1 cells but not to JAM-Cneg K1718 cells. Pre-incubation with anti-alpha-4 integrin antibody did not affect this binding; however, incubation with anti-JAM-C antibody inhibited the binding of soluble JAM-B Fc by 66% (FIG. 5E). Similar results were obtained with JAM-Cpos transfected Raji cells, where pre-incubation with anti-alpha-4 integrin antibody did not influence the binding of soluble JAM-B Fc (FIG. 13C).

Figure 6:
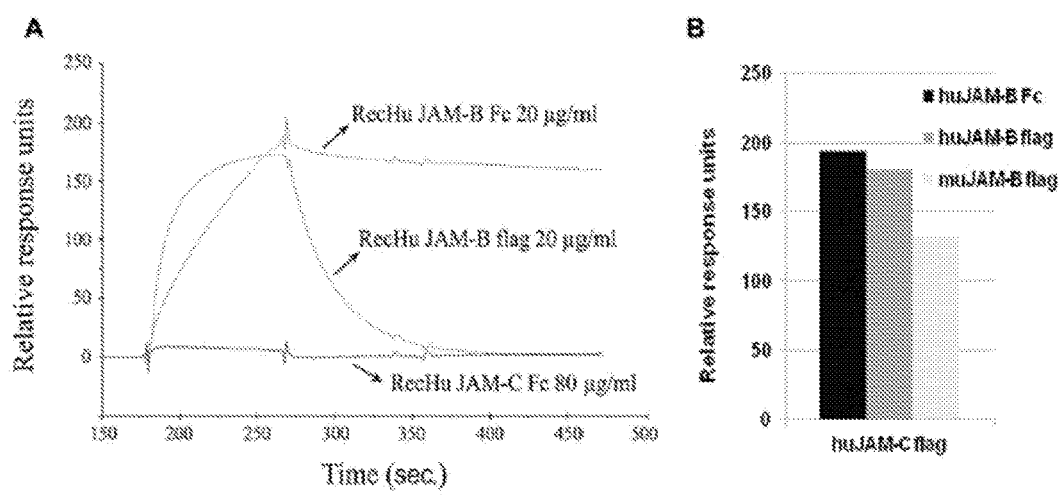
FIGS. 6A-B: Analysis of JAM-B/JAM-C interactions with Surface Plasmon Resonance.

Example 5—Surface Plasmon Resonance Identifies JAM-B but not JAM-C as a Ligand for JAM-C To confirm the specificity of the JAM-C/JAM-B interaction at the molecular level, soluble human JAM-C-FLAG protein was covalently immobilized to a Biacore CM5 sensor chip Immobilization was assessed by testing the binding of anti-JAM-C monoclonal and polyclonal antibodies. Under these conditions, soluble recombinant JAM-B Fc and JAM-B FLAG bound to immobilized JAM-C, demonstrating a clear JAM-B/JAM-C interaction, while binding of soluble JAM-C Fc to immobilized JAM-C was not detected (FIG. 6A). JAM-B FLAG was observed to dissociate rapidly, whereas the JAM-B Fc interaction with JAM-C remained stable. This kinetic pattern may be due to the dimeric form of the Fc-tagged molecule forming a more stable interaction with JAM-C than the monomeric form of JAM-B FLAG. Homotypic JAM-C/JAM-C interaction was never observed under these conditions, even when injecting higher concentrations of JAM-C Fc. This suggests that the JAM-C/JAM-B interaction is of much higher affinity than JAM-C/JAM-C binding. To validate these findings for the model of human cells injected into mice, the inventors subsequently confirmed that human JAM-C binds to murine JAM-B to the same extent as to human JAM-B (FIG. 6B). Thus, both the cell adhesion and SPR data show that human and mouse JAM-B are ligands for JAM-C expressed by human B cells.

Interaction studies were performed on a Biacore 2000 (GE Healthcare). Recombinant proteins were immobilized at a concentration of 5 µg/mL on a CM5 sensor chip using the amine coupling kit (NHS-EDC) provided by the Biacore supplier. Background signal from a reference channel without soluble JAM-C was automatically subtracted. Proteins (30 µL) were injected (Kinject) in running buffer (400 µM Tris-HCl pH 7.4, containing 145 mM NaCl) at a flow rate of 20 µL/min.

Figure 14:
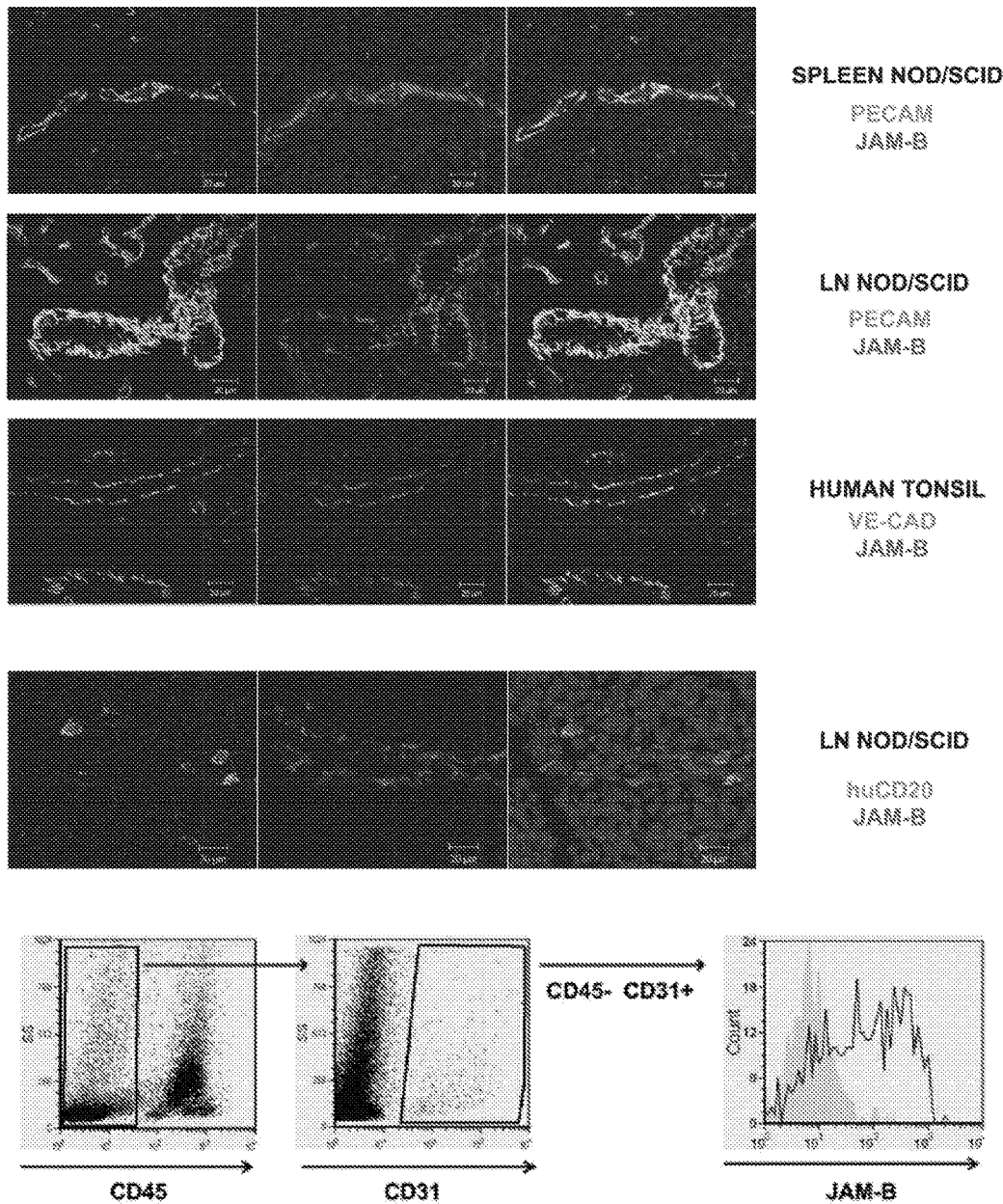
FIG. 14: JAM-B is expressed on endothelial cells from humans and NOD/SCID mice and interact with JAM-Cpos cells. Immunofluorescence was performed on cryosections from spleen and lymph nodes (LN) of NOD-SCID mice and on cryosections from human tonsil, using a rabbit anti-JAM-B affinity purified polyclonal antibody. JAM-C expressing human B cells were detected with an anti-human CD20 antibody. On BM, cell surface expression of JAM-B was assessed by flow cytometry using a rabbit anti-mouse JAM-B affinity-purified polyclonal antibody followed by the staining of cells with directly conjugated anti-mouse CD45-PC7 and anti-mouse PECAM-PE. Endothelial cells were gated as CD45neg and PECAMpos.

Example 6—Vascular Endothelial Cells in Lymphoid Tissues Express JAM-B and Interact with JAM-C Positive B Cells JAM-B has been localized in cell-cell junctions of blood vessels, including high endothelial venules (HEV) in lymph nodes of normal mice (Pfeiffer et al., 2008). In addition, the presence of JAM-B in murine bone marrow endothelial cells has been confirmed by flow cytometry and immunofluorescence (Arcangeli et al., 2011). To ensure that JAM-B is also expressed by endothelial cells in NOD/SCID mice, LN and spleen sections were stained for JAM-B, and BM was analyzed by flow cytometry for the presence of JAM-B-positive endothelial cells. JAM-B co-localized with PECAM-1 on blood vessels in spleen and LNs, and CD45neg, PECAMpos BM endothelial cells stained positive for JAM-B (FIG. 14). To extend these results to humans, JAM-B staining on human lymphoid tissue was carried out. Co-localization of JAM-B and endothelial specific VE-Cadherin (VE-CAD) was observed in the vasculature of human tonsils. Double staining experiments were carried out to determine the localization of JAM-Cpos B cells in relation to JAM-B-expressing endothelial cells of blood vessels.

Lymph nodes of NOD/SCID mice, injected with JAM-Cpos human B cells, were collected one hour after injection and stained with anti-human CD20 and anti-mouse JAM-B antibodies. Immunofluorescence was performed on cryosections from LNs of NOD/SCID mice obtained one hour after the inoculation of human B cells. Human B cells were found adjacent to JAM-Bpos endothelial cells (FIG. 14).

To analyze the expression of JAM-B on murine endothelial BM cells, femur and tibia were dissected, crushed, and digested in PBS containing 2 mg/mL collagenase (Sigma-Aldrich) for 45 min. After washing and filtering the cells through a 50 μm cell strainer (BD Bioscience), expression of JAM-B was assessed by flow cytometry using the rabbit anti-mouse JAM-B affinity-purified polyclonal antibody (1/1000), followed by the staining of cells with directly conjugated anti-mouse CD45-PC7 and anti-mouse PECAM-PE (eBioscience). Cells were incubated for 20 min at RT, washed, and analyzed by flow cytometry as described above.

For immunofluorescence staining, 5 μm cryosections were obtained from the spleen and LNs of injected mice and from human tonsils. Sections were fixed in cold methanol-acetone for 5 min, dried, and rehydrated in 0.1% BSA-PBS for 15 min at RT. Mouse samples were incubated for 1 hour with rabbit anti-mouse JAM-B affinity-purified polyclonal antibody (1/100, obtained after immunization with a murine JAM-B-FLAG fusion protein) and rat anti-mouse PECAM-1 antibody GC51 (1 μg/mL) (Piali et al., 1995) or mouse anti-human CD20 antibody (clone L26, Dako). Tonsil sections were incubated with rabbit anti-human JAM-B affinity purified antibody (1/100) and mouse anti-human VE-CAD 55-7H1 (BD Biosciences). Sections were washed 3×5 min at room temperature and incubated for an additional hour with affinity-purified DyLight 649 F(ab)2 donkey anti-rabbit, DyLight 488 F(ab)2 donkey anti-rat (Jackson Laboratories), and human serum-adsorbed, DyLight 488 goat anti-mouse antibodies (KPL). Nuclei were counterstained with DAPI (200 ng/mL, Invitrogen), slides were mounted in Moewiol (Sigma-Aldrich), and fluorescence was scanned on a LSM 510Meta confocal microscope (Carl Zeiss).

Example 7—Decreased Lymphoma Engraftment by Anti-JAM-C Antibody Treatment

Figure 7:
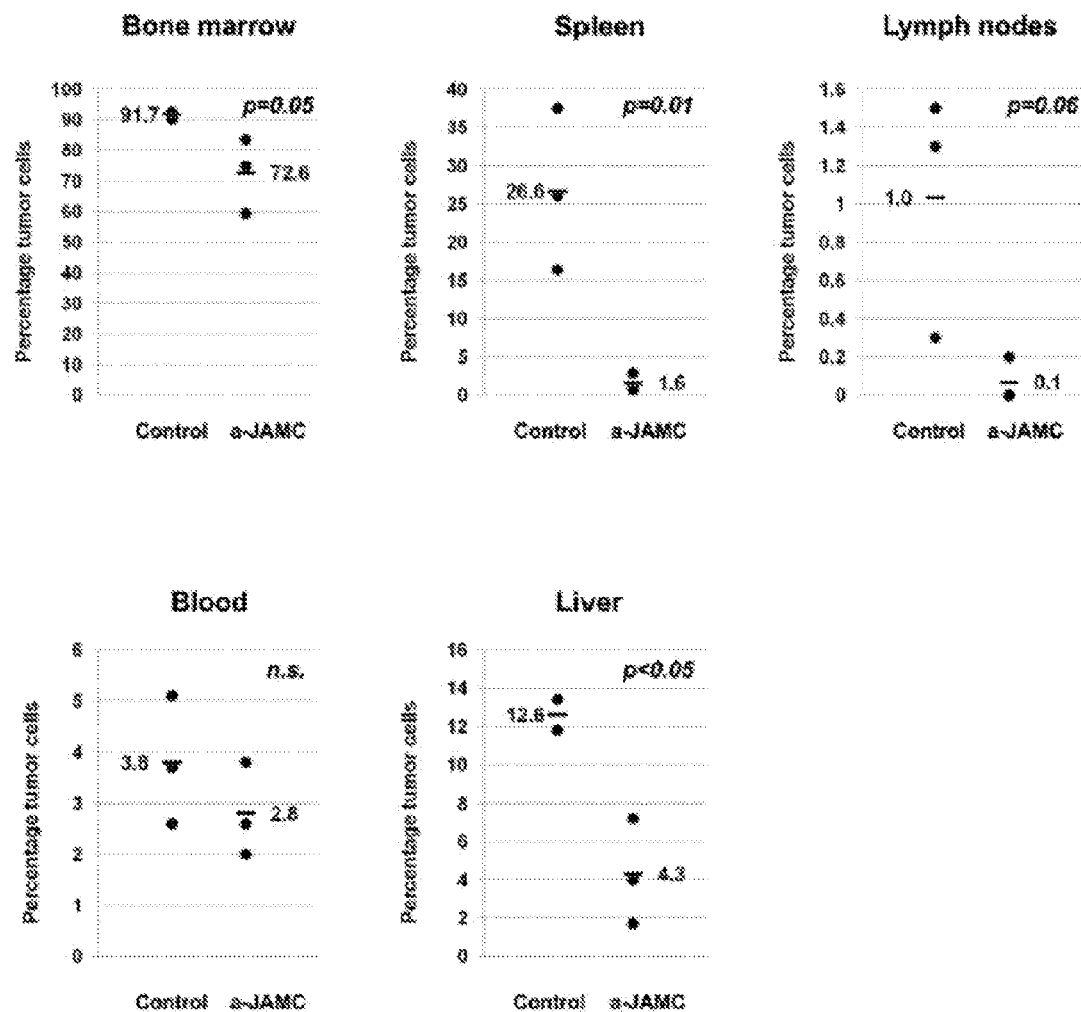
FIG. 7: Effect of anti-JAM-C treatment on long-term B-cell lymphoma engraftment. Jeko-1 cells ($5\times10^6$ cells) were injected into the tail vein of NOD/SCID mice. Animals were treated with rabbit anti-JAM-C antibodies or with rabbit IgG during three weeks. At day 24, mice were sacrificed and BM, spleen, LNs, blood, and liver were analyzed by flow cytometry for the presence of Jeko-1 cells, using anti-CD19 and anti-CD45 antibodies. Anti-JAM-C treatment reduced JAM-Cpos Jeko-1 lymphoma engraftment in BM, spleen, LNs, and liver. One representative experiment (three mice per group) out of two is shown. Differences in the Jeko-1 percentages between antibody treated and control mice were analyzed using Student's t-test.

To study whether the effect of anti-JAM-C antibody on B cell homing observed in the short-term assays could be translated into a clinically-relevant effect for lymphoma treatment, long-term assays were performed. The JAM-Cpos B cell line Jeko-1 (Jeon et al., 1998) was injected into the tail veins of NOD/SCID mice. Animals were treated for three weeks with either anti-JAM-C antibody or with control IgG (10 μg/mouse, two times per week), and tumor burdens were evaluated on day 24. The percentage of Jeko-1 cells recovered from the BM, spleen, LNs, and liver of anti-JAM-C-treated mice was significantly reduced compared to control animals by 21%, 94%, 90%, and 66%, respectively (FIG. 7). No significant difference was found in the percentage of Jeko-1 cells recovered from peripheral blood. These results demonstrate that anti-JAM-C antibody treatment not only inhibited homing of B cells to lymphoid organs, but also reduced long-term lymphoma engraftment.

For long-term assays in NOD/SCID mice, Jeko-1 cells ($5\times10^6$ cells) were injected intravenously into 4-8 week-old NOD/SCID mice. Twenty-four hours after the injection, mice were treated with either rabbit IgG (control group) or anti-JAM-C antibody (10 μg/mouse). Subsequently, antibodies were administrated intravenously two times per week for three weeks. Mice were monitored for general condition and weight loss, and sacrificed at day 24. Blood, liver, BM, spleen, and LNs were collected and analyzed for the presence of Jeko-1 cells by flow cytometry using human-specific anti-CD45 and anti-CD19 antibodies.

Figure 15:
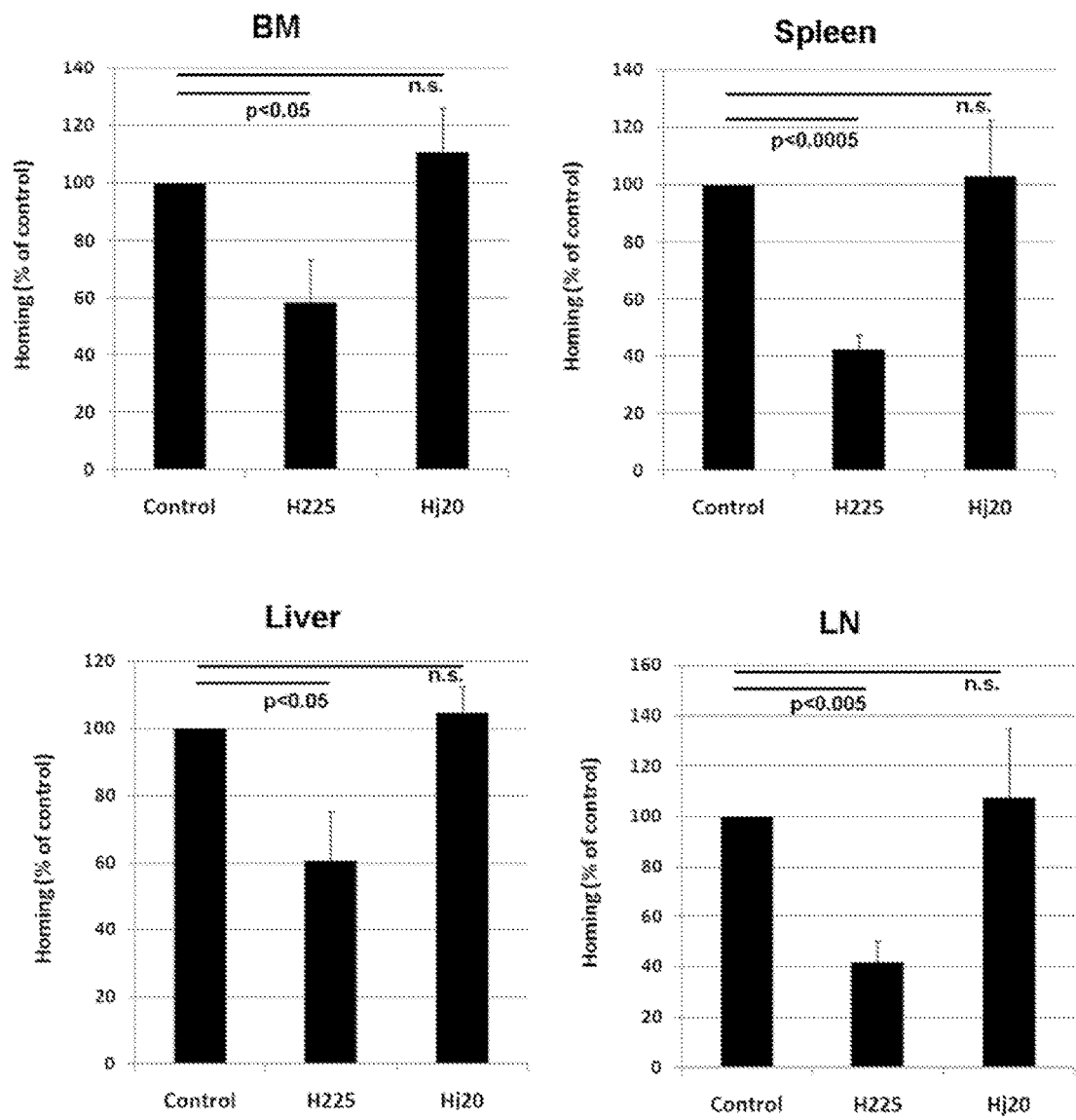
FIG. 15: Distribution of normal B cells treated with monoclonal anti-JAM-C IgG1 antibodies. FACS analysis of the homing pattern of normal B cells treated with anti-JAM-C monoclonal antibodies. Normal human B cells, either incubated for 30 min with control IgG1, either anti-JAM-C Hj20 monoclonal antibody or anti-JAM-C H225 monoclonal antibody, were injected into NOD/SCID mice. One hour after injection the mice were sacrificed and organs were analyzed. The number of B cells was quantified as the number of CD45pos-CD19pos cells per 10$^6$ total acquired cells by FACS, per 10$^6$ injected B cells. Effect of anti-JAM-C antibody on the homing of human B cells to liver, BM, spleen, and LNs, compared to control (control=100%). Data are mean±SEM from four independent experiments.
Figure 16:
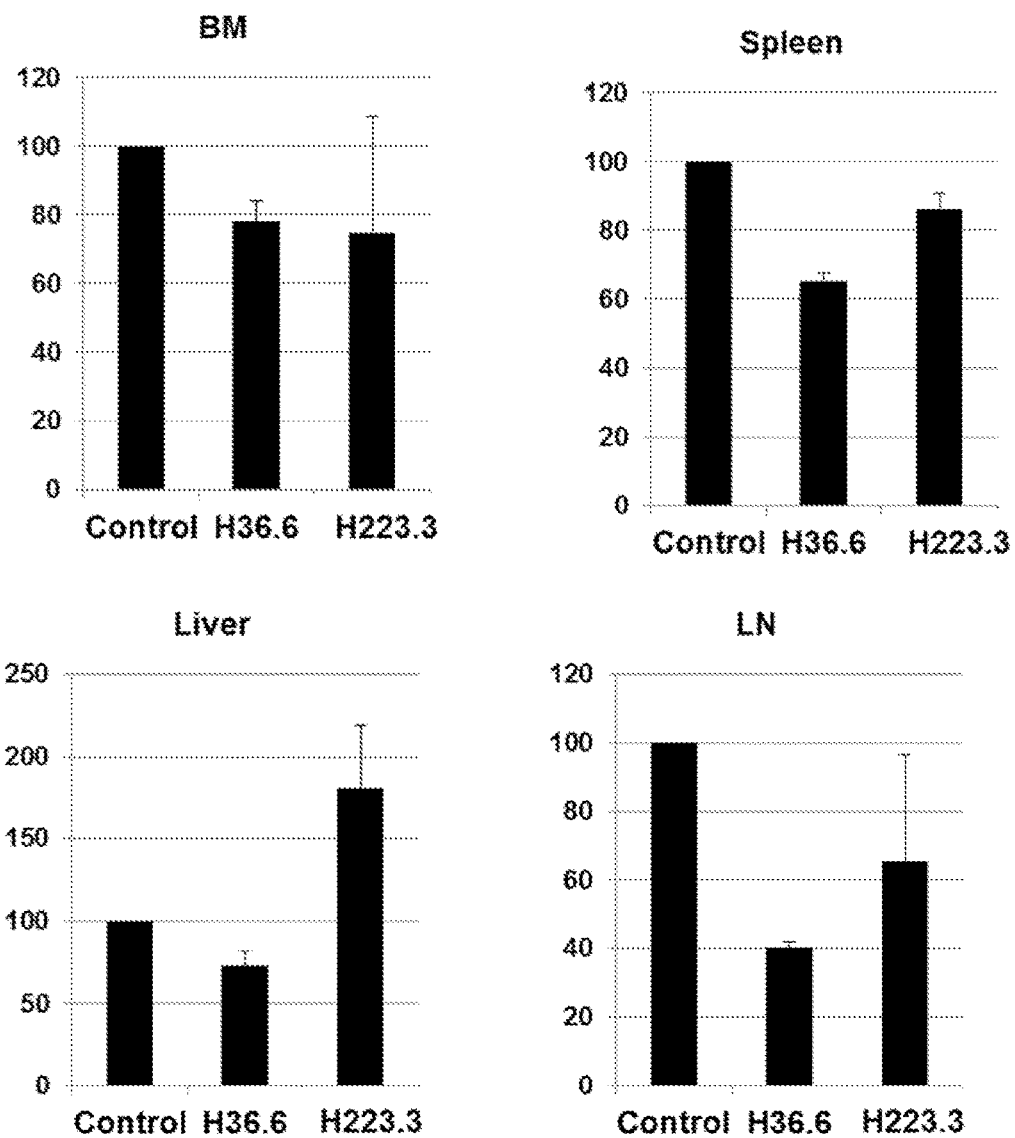
FIG. 16: Distribution of normal B cells treated with monoclonal anti-JAM-C IgG2 antibodies. FACS analysis of the homing pattern of normal B cells treated with anti-JAM-C monoclonal antibodies. Normal human B cells, incubated for 30 min with control IgG2, anti-JAM-C monoclonal H36.6 antibody, or anti-JAM-C monoclonal H223.3 antibody, were injected into NOD/SCID mice. One hour after injection the mice were sacrificed and organs were analyzed. The number of B cells was quantified as the number of CD45pos-CD19pos cells per 10$^6$ total acquired cells by FACS, per 10$^6$ injected B cells. Effect of anti-JAM-C antibody on the homing of human B cells to liver, BM, spleen, and LNs, compared to control (control=100%). Data are mean±SEM from two independent experiments.
Figure 17:
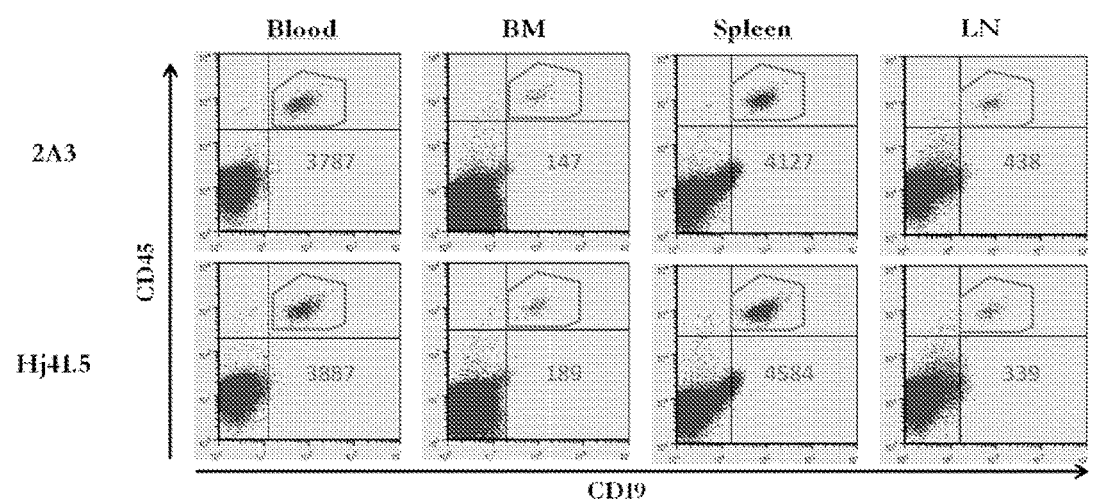
FIG. 17: Homing of normal human B cells to lymphoid organs is not reduced by anti-JAM-C monoclonal antibody Hj41.5. Normal human B cells, either incubated for 30 min with control IgG or with anti-JAM-C Hj41.5 monoclonal antibody, were injected into NOD/SCID mice. One hour after injection the mice were sacrificed and bone marrow (BM), spleen, lymph nodes (LN), and blood were analyzed by flow cytometry for the presence of human B cells, using anti-CD19 and anti-CD45 antibodies. Results of one experiment are shown. Gates indicate the number of human B cells recovered from BM, spleen, LN, and blood, expressed as number of detected B cells per $10^6$ cells acquired by flow cytometry per $10^6$ B cells injected into the mice.

Example 8—Short-Term In Vivo Homing is Blocked by Anti-JAM-C Monoclonal Antibodies Normal human B cells were incubated with monoclonal anti-JAM-C antibody or an isotype control for 30 min and then tested for in vivo homing in NOD/SCID mice. One hour after injection, the mice were sacrificed and the organs were analyzed by FACS analysis for CD45pos and CD19pos cells. The number of B cells was quantified as the number of CD45pos-CD19pos cells per $10^6$ total acquired cells per $10^6$ injected B cells. Four monoclonal antibodies were tested: H225 (IgG1), Hj20 (IgG1), H36.6 (IgG1) and H223.3 (IgG2). Antibody H225 was found to decrease homing to the spleen by 63% compared to the control, while antibodies Hj20 and H223.3 were found to decrease homing to the spleen by only 16% and 14%, respectively (FIGS. 15 and 16). Likewise, H225 decreased homing to the bone marrow, liver, and lymph nodes to a greater extent than Hj20 and H223.3. Antibody Hj41.5 failed to block homing of normal human B cells (FIG. 17).

The $V_H$ and $V_L$ chains of antibodies H225 (SEQ ID NO: 4 and 5), Hj20 (SEQ ID NO: 6 and 7), H223.3 (SEQ ID NO: 8 and 9), and Hj41.5 (SEQ ID NO: 10 and 11) were sequenced and the complementarity determining regions (CDRs) determined Total RNA was extracted from the hybridoma cell pellets and cDNA was created from the RNA by reverse-transcription with an oligo(dT) primer. PCR reactions using variable domain primers to amplify both the $V_H$ and $V_L$ regions of the monoclonal antibody DNA were performed. The products were extracted and gel purified and then cloned into the Invitrogen sequencing vector pCR2.1 and transformed into TOP10 for positive transformants. Selected colonies were picked and analyzed through sequencing, from which a consensus sequence for each antibody was generated (Table 1). The CDRs were determined by the IMGT numbering system (Lefranc et al., 1999).

Antibody H225 comprises $V_H$ CDR sequences corresponding to SEQ ID NOs: 12, 13, and 14 and $V_L$ CDR sequences corresponding to SEQ ID NOs: 15, 16, and 17. Antibody Hj20 comprises $V_H$ CDR sequences corresponding to SEQ ID NOs: 18, 19, and 20 and $V_L$ CDR sequences corresponding to SEQ ID NOs: 21, 22, and 23. Antibody Hj223.3 comprises $V_H$ CDR sequences corresponding to SEQ ID NOs: 24, 13, and 25 and $V_L$ CDR sequences corresponding to SEQ ID NOs: 15, 16, and 17. Antibody Hj41.5 comprises $V_H$ CDR sequences corresponding to SEQ ID NOs: 24, 26, and 27 and $V_L$ CDR sequences corresponding to SEQ ID NOs: 28, 29, and 30.

Figure 18:
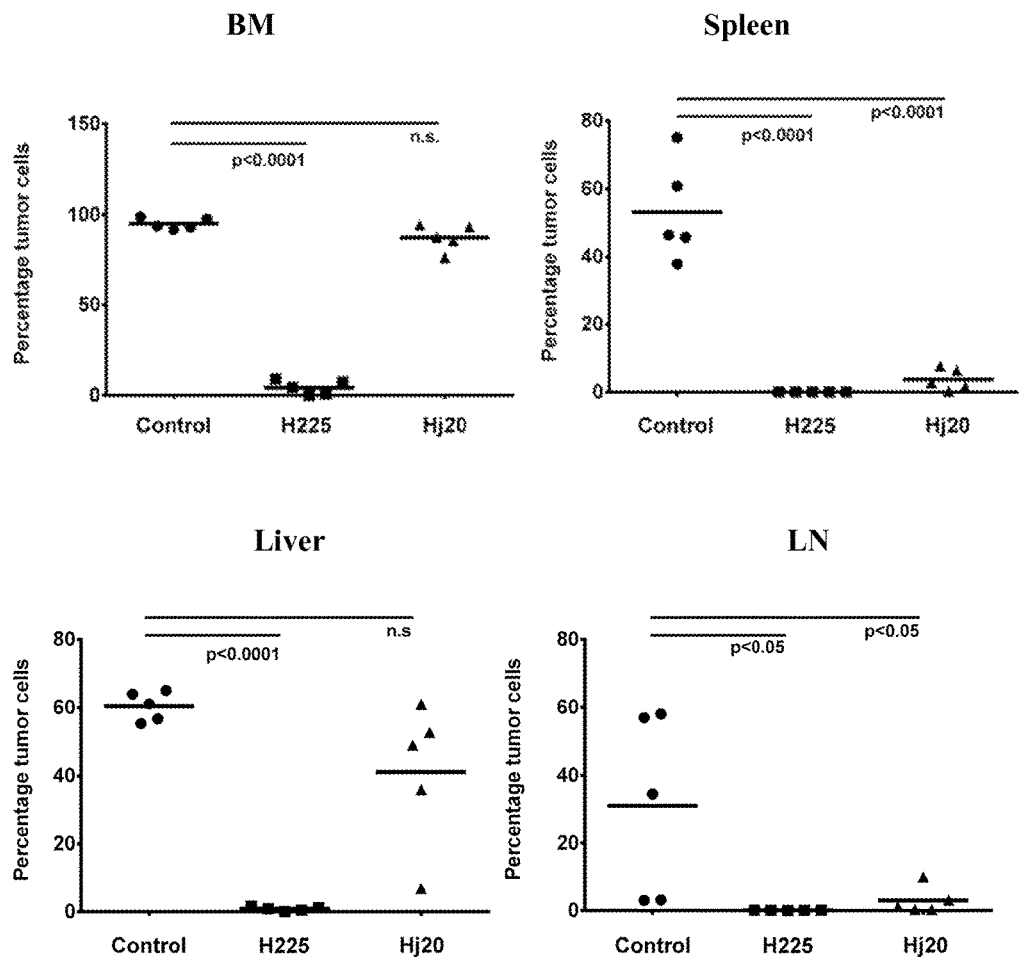
FIG. 18: Effect of monoclonal anti-JAM-C antibodies on long-term B-cell lymphoma engraftment. Jeko-1 cells ($5\times10^6$ cells) were injected into the tail vein of NOD/SCID mice. Animals were treated with monoclonal anti-JAM-C antibodies or with control IgG1 during three weeks. At day 26, mice were sacrificed and BM, spleen, LNs and liver were analyzed by flow cytometry for the presence of Jeko-1 cells, using anti-CD19 and anti-CD45 antibodies. Anti-JAM-C treatment with H225 antibody reduced JAM-Cpos Jeko-1 lymphoma engraftment in BM, spleen, LNs, and liver. Anti-JAM-C treatment with Hj20 antibody reduced JAM-Cpos Jeko-1 lymphoma engraftment in spleen and LNs. Differences in the Jeko-1 percentages between antibody treated and control mice were analyzed using ANOVA, followed by Bonferroni post-hoc analysis, P<0.05.

Example 9—Decreased Lymphoma Engraftment by Monoclonal Anti-JAM-C Antibodies Treatment To study the effect of monoclonal anti-JAM-C antibodies on lymphoma B cell dissemination, long-term assays were performed. The JAM-Cpos B cell line Jeko-1 was injected into the tail veins of NOD/SCID mice. Animals were treated for three weeks with either control IgG1, either anti-JAM-C Hj20 monoclonal antibody or anti-JAM-C H225 monoclonal antibody (50 μg/mouse, two times per week), and tumor burdens were evaluated on day 26. The percentage of Jeko-1 cells recovered from the spleen and LNs of mice treated with anti-JAM-C Hj20 monoclonal antibody was reduced compared to control animals by 93% and 98%, respectively (FIG. 18). No differences were found in the percentage of tumor cells present in BM or liver. In mice treated with anti-JAM-C H225 monoclonal antibody, the percentage of Jeko-1 cells recovered from the BM, spleen, LNs, and liver was significantly reduced compared to control animals by 95%, 100%, 99%, and 100%, respectively (FIG. 18). These results demonstrate that anti-JAM-C antibody treatment not only inhibited homing of B cells to lymphoid organs, but also reduced long-term lymphoma engraftment.

For long-term assays in NOD/SCID mice, Jeko-1 cells ($5 \times 10^6$ cells) were injected intravenously into 4-8 week-old NOD/SCID mice. Six days after the injection, mice were treated with either IgG1 (control group), either anti-JAM-C Hj20 monoclonal antibody or anti-JAM-C H225 monoclonal antibody (50 μg/mouse). Subsequently, antibodies were administrated intravenously two times per week for three weeks. Mice were monitored for general condition and weight loss, and sacrificed at day 26. Blood, liver, BM, spleen, and LNs were collected and analyzed for the presence of Jeko-1 cells by flow cytometry using human-specific anti-CD45 and anti-CD19 antibodies.

Example 10—Anti-JAM-C Antibodies Decrease B Cell Proliferation

Figure 19A:
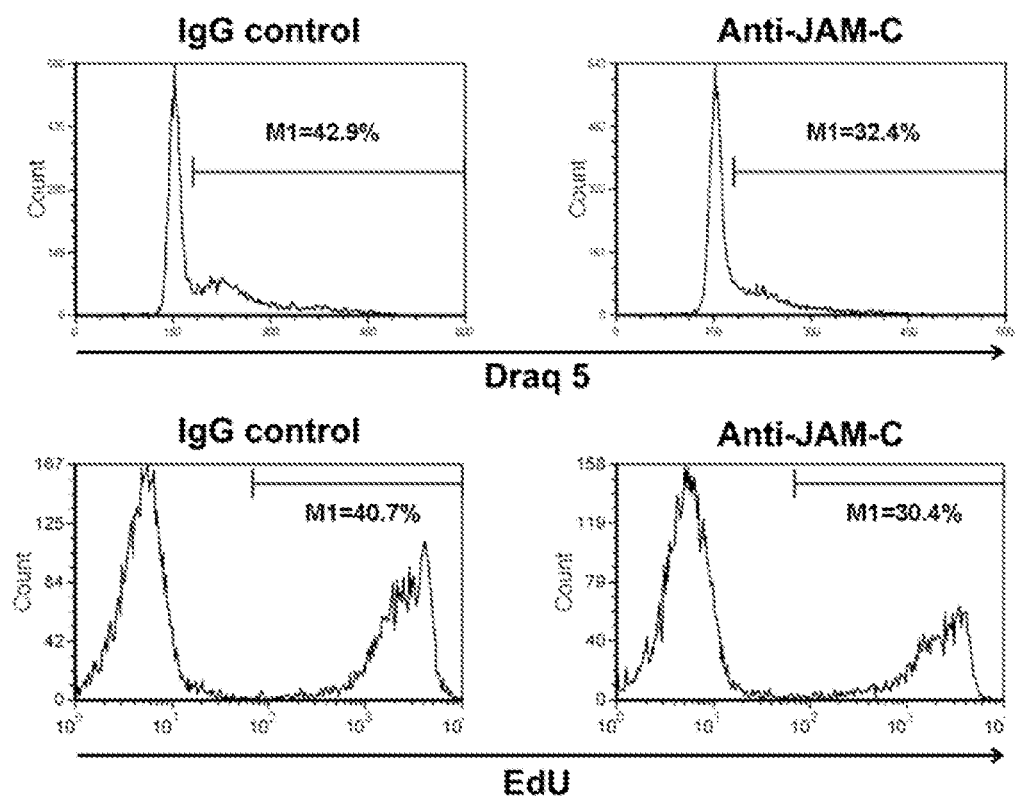
FIGS. 19A-D: Anti-JAM-C mAb reduces the proliferation of normal and malignant JAM-Cpos B cells.
Figure 19B:
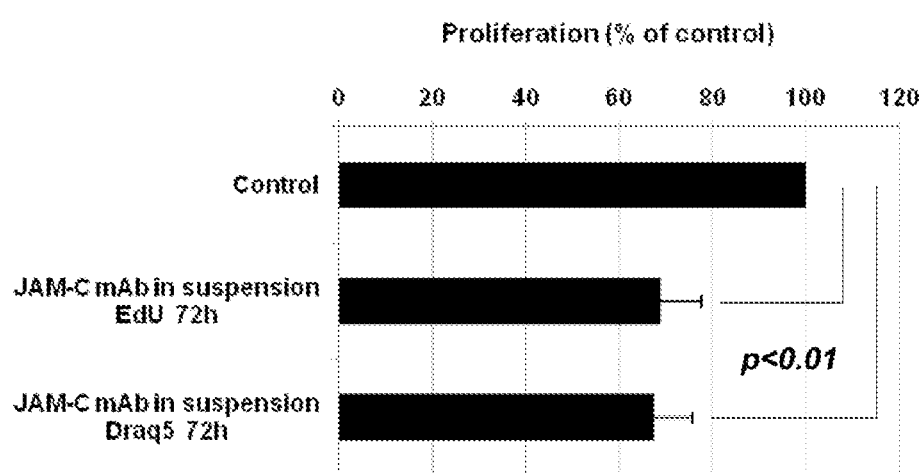
Figure 19C:
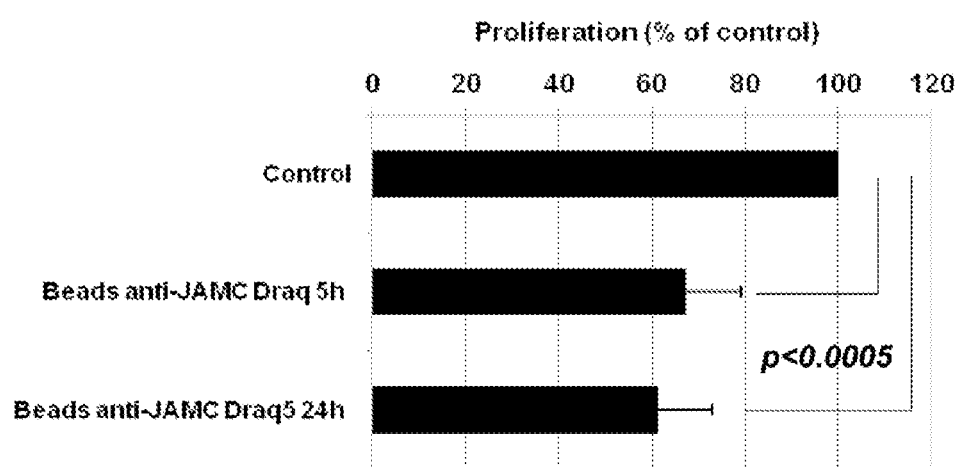
Figure 19D:
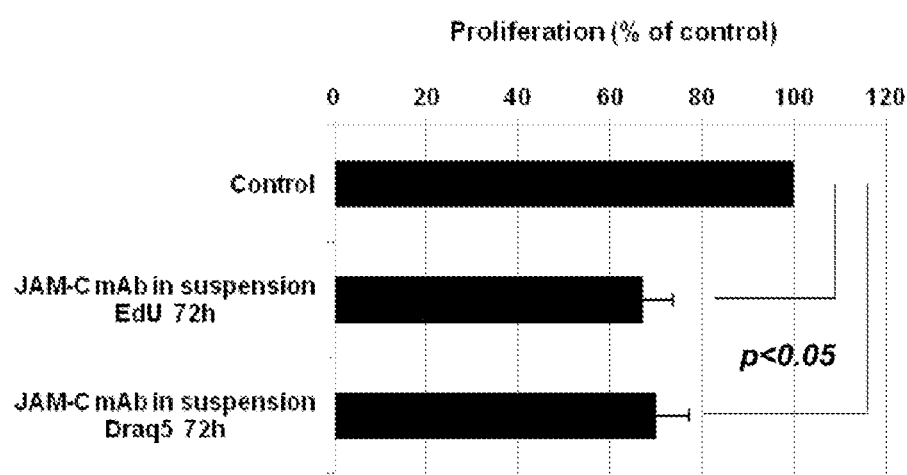

Samples of JAM-Cpos normal and lymphoma cells were cultured with CD40L and cytokines and with either a control IgG (10 μg/mL) or a JAM-C mAb (10 μg/mL). Proliferation was quantified by flow cytometry using Draq5 and EdU-staining. Treatment with JAM-C mAb reduced the number of proliferating cells by about 25% (FIG. 19A). The normal B cells were cultured with either JAM-C mAb in suspension or bead-bound anti-JAM-C mAb. The JAM-Cpos lymphoma cells were cultured with JAM-C mAB in suspension. Anti-JAM-C mAb reduced the proliferation of both normal and malignant JAM-Cpos B cells (FIGS. 19B-D).

Figure 20A:
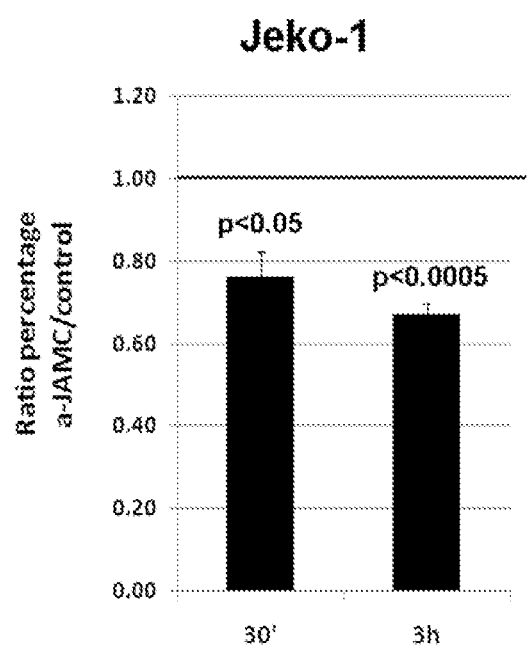
FIGS. 20A-C: Anti-JAM-C mAb decreases phosphorylation of ERK1/2.
Figure 20B:
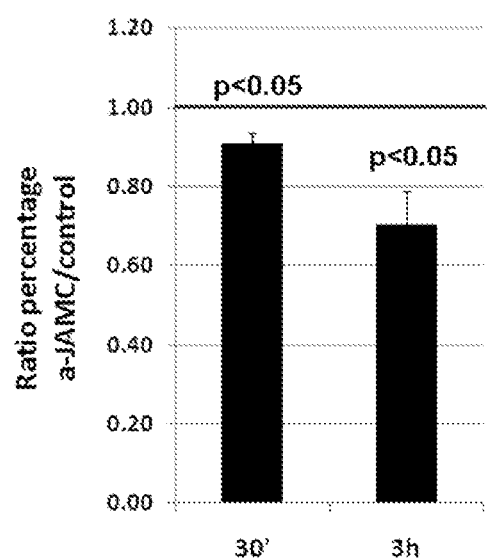

To understand this effect on proliferation, the inventors assayed the level of ERK phosphorylation in Jeko-1 cells, primary B cells, and primary JAM-Cpos lymphoma cells treated with anti-JAM-C mAb. Primary B cells and primary JAM-Cpos lymphoma cells were activated with CD40L and cytokines. In Jeko-1 cells and primary B cells, treatment for 30 min and 3 h resulted in a statistically significant reduction in phospho-ERK levels (FIGS. 20A and B). In primary

TABLE 1

Antibody sequences.

| mAb | Heavy Chain Sequence | | | Light Chain Sequence | | |
|---|---|---|---|---|---|---|
| | CDR1 | CDR2 | CDR3 | CDR1 | CDR2 | CDR3 |
| | Amino acid sequence | | | Amino acid sequence | | |
| IgG1 | | | | | | |
| H225 | GYTFTSFY (SEQ ID NO: 12) | INTGSGGT (SEQ ID NO: 13) | ARDNSGYVLDY (SEQ ID NO: 14) | QNINRY (SEQ ID NO: 15) | NAN (SEQ ID NO: 16) | LQYNSWPLT (SEQ ID NO: 17) |
| | QVQLQQSGAELAKPGSSVKISCKASGY TFTSFYINWLKQTTGQGLEYIGYINTG SGGTNYNEKFKGKATLTVDKSSTAFM QLSSLTPDDSAVYYCARDNSGYVLDYW GQGVMVTVSS (SEQ ID NO: 4) | | | DIQMTQSPSFLSASVGDRVTINCKASQ NINRYLNWYQEKVGEAPKLLIYNANSL QTGIPSRFSGSGSGTDFTLTISSLQPE NVATYFCLQYNSWPLTFGSGTKLEIK (SEQ ID NO: 5) | | |
| Hj20 | GYTFTSYD (SEQ ID NO: 18) | IYPGNGNT (SEQ ID NO: 19) | ARGDGVDY (SEQ ID NO: 20) | QNINKY (SEQ ID NO: 21) | KTN (SEQ ID NO: 22) | FQYNSGPRT (SEQ ID NO: 23) |
| | QVQLQQSGAELAKPGSSVKISCKASGY TFTSYDMHWIKQQPGNGLEWIGWIYPG NGNTRYNQKFNGKATLTADKSSTAHM QLGSLTSEDSAVYFCARGDGVDYWGQG VMVTVSS (SEQ ID NO: 6) | | | DIQMTQSPSFLSASVGDRVTITCKASQ NINKYLNWYQQKLGEAPKRLIYKTNSL QTGIPSRFSGSGSGTDYTLTISSLQPE DVATYFCFQYNSGPRTFGGGTKLEI (SEQ ID NO: 7) | | |
| IgG2 | | | | | | |
| Hj223.3 | GYTFTSYY (SEQ ID NO: 24) | INTGSGGT (SEQ ID NO: 13) | ARDEDTTPFDY (SEQ ID NO: 25) | QNINRY (SEQ ID NO: 15) | NAN (SEQ ID NO: 16) | LQYNSWPLT (SEQ ID NO: 17) |
| | QVQLQQSGAELAKPGSSVKISCKASGY TFTSYYISWIKQTTGQGLDFIGYINTG SGGTNYNEKFKGKATLTVDKSSNTAFM QLSSLTPDDSAVYYCARDEDTTPFDYW GQGVMVTVSS (SEQ ID NO: 8) | | | DIQMTQSPSFVSASVGDRVTINCKASQ NINRYLNWYQQKLEEAPKLLIYNANSL QTGIPSRFSGSGSGTDFTLTISSLQPE DVATYFCLQYNSWPLTFGSGTKLEIK (SEQ ID NO: 9) | | |
| IgG2a | | | | | | |
| Hj41.5 | GYTFTSYY (SEQ ID NO: 24) | ISTGSGSA (SEQ ID NO: 26) | ARRDTIAVLAY (SEQ ID NO: 27) | CRASESVSTL (SEQ ID NO: 28) | LAS (SEQ ID NO: 29) | HQSWNDPYT (SEQ ID NO: 30) |
| | QVQLQQSGAELAKPGSSVKISCKASGY TFTSYYISWIKQTTGQGLEYIGFISTG SGSANYNEKFKGKATFTVDKSSTAFM QLSSLRPDDSAVYYCARRDTIAVLAYW GQGTLVTVSS (SEQ ID NO: 10) | | | DIVLTQSPALAVSPGERVTISCRASES VSTLMHWYQQKPGQQPKLLIYLASHLE SGVPAKFSGSGSGTDFTLTIDPVEADD TATYYCHQSWNDPYTFGAGTKLELK (SEQ ID NO: 11) | | |

Figure 20C:
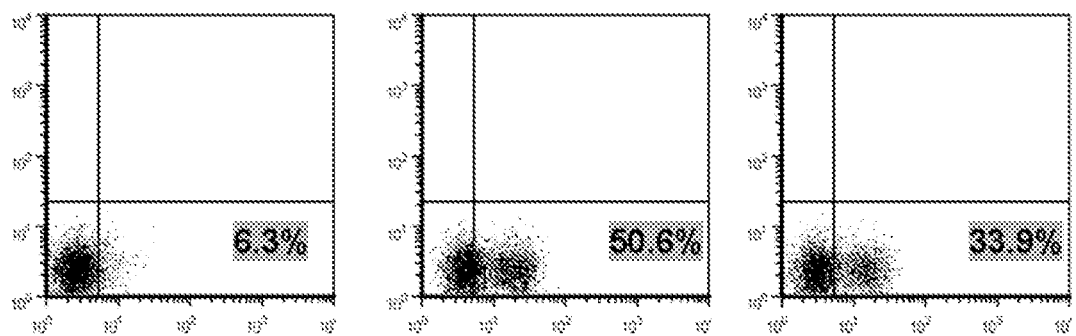

JAM-Cpos lymphoma cells, treatment with anti-JAM-C mAb resulting in a reduction of phospho-ERK levels from 50.6% to 33.9% (FIG. 20C).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,469,797
U.S. Pat. No. 4,472,509
U.S. Pat. No. 4,606,855
U.S. Pat. No. 4,703,003
U.S. Pat. No. 4,742,159
U.S. Pat. No. 4,767,720
U.S. Pat. No. 4,816,567
U.S. Pat. No. 4,867,973
U.S. Pat. No. 4,870,287
U.S. Pat. No. 4,938,948
U.S. Pat. No. 4,946,778
U.S. Pat. No. 5,021,236
U.S. Pat. No. 5,091,513
U.S. Pat. No. 5,164,296
U.S. Pat. No. 5,196,066
U.S. Pat. No. 5,223,409
U.S. Pat. No. 5,403,484
U.S. Pat. No. 5,420,253
U.S. Pat. No. 5,565,332
U.S. Pat. No. 5,571,698
U.S. Pat. No. 5,627,052
U.S. Pat. No. 5,656,434
U.S. Pat. No. 5,739,169
U.S. Pat. No. 5,760,395
U.S. Pat. No. 5,770,376
U.S. Pat. No. 5,789,208
U.S. Pat. No. 5,801,005
U.S. Pat. No. 5,821,337
U.S. Pat. No. 5,824,311
U.S. Pat. No. 5,830,880
U.S. Pat. No. 5,844,091
U.S. Pat. No. 5,846,945
U.S. Pat. No. 5,858,657
U.S. Pat. No. 5,861,155
U.S. Pat. No. 5,871,907
U.S. Pat. No. 5,969,108
U.S. Pat. No. 6,054,297
U.S. Pat. No. 6,165,464
U.S. Pat. No. 6,365,157
U.S. Pat. No. 6,406,867
U.S. Pat. No. 6,709,659
U.S. Pat. No. 6,709,873
U.S. Pat. No. 6,753,407
U.S. Pat. No. 6,814,965
U.S. Pat. No. 6,849,259
U.S. Pat. No. 6,861,572
U.S. Pat. No. 6,875,434
U.S. Pat. No. 6,881,557
U.S. Pat. No. 6,891,024
U.S. Pat. No. 6,946,546
U.S. Patent Publn. 2002/0172677
U.S. Patent Publn. 2004/0126828
U.S. Patent Publn. 2005/0214860
U.S. Patent Publn. 2005/0136060
Arcangeli et al., *Blood*, 118:4609-19, 2011.
Arrate et al., *J. Biol. Chem.*, 276:45826-32, 2001.
Austin-Ward and Villaseca, *Revista Medica de Chile*, 126(7):838-845, 1998.
Barbas et al., *Proc. Natl. Acad. Sci., USA*, 91:3809-3813, 1994.
Berlin-Rufenach et al., *J. Exp. Med.*, 189:1467-78, 1999.
Bertrand et al., *Immunol Rev.*, 175:175-86, 2000.
Bradfield et al., *Arterioscler Thromb Vasc Biol.*, 27:2104-12, 2007.
Bukowski et al., *Clinical Cancer Res.*, 4(10):2337-2347, 1998.
Burger et al., *Blood*, 114:3367-75, 2009.
Christodoulides et al., *Microbiology*, 144(Pt 11):3027-3037, 1998.
Coupland, *Histopathology*, 58:69-80, 2011.
Cunningham et al., *J. Biol. Chem.*, 277:27589-92, 2002.
Cyster, *Immunol. Rev.*, 194:48-60, 2003.
Davidson et al., *J. Immunother.*, 21(5):389-398, 1998.
Gram et al., *Proc. Natl. Acad. Sci. USA*, 89:3576-3580, 1992.
Hanibuchi et al., *Int. J. Cancer*, 78(4):480-485, 1998.
Hartmann et al., *Cancer Res.*, 69:3121-30, 2009.
Hellstrand et al., *Acta Oncologica*, 37(4):347-353, 1998.
Hollander, *Front. Immun.*, 3:3, 2012.
Hu et al., *Cancer Res.*, 56:3055-3061, 1996.
Hui and Hashimoto, *Infection Immun.*, 66(11):5329-5336, 1998.
Jeon et al., *Br. J. Haematol.*, 102:1323-6, 1998.
Jin et al., *Nature Medicine*, 12:1167-74, 2006.
Koni et al., *J. Exp. Med.*, 193:741-54, 2001.
Kraal et al., *Am. J. Pathol.*, 147:763-71, 1995.
Lapidot and Kollet, *Leukemia*, 16:1992-2003, 2002.
Lefranc et al., *Nuc. Acids Res.*, 27:209-212, 1999.
Li et al., *Arterioscler. Thromb. Vasc. Biol.*, 29:1200-6, 2009.
Liang et al., *J. Immunol.*, 1618-26, 2002.
Liu et al., *Cell Mol. Biol.*, 49:209-216, 2003.
Lo et al., *J. Exp. Med.*, 197:353-61, 2003.
Luster et al., *Nature Immunol.*, 6:1182-90, 2005.
Marks et al., *Bio/Technol.*, 10:779-783, 1992.
Matsunaga et al., *Nature Medicine*, 9:1158-65, 2003.
Mitchell et al., *Ann. NY Acad. Sci.*, 690:153-166, 1993.
Mitchell et al., *J. Clin. Oncol.*, 8(5):856-869, 1990.
Miyasaka and Tanaka, *Nat. Rev. Immunol.*, 4:360-70, 2004.
Mori et al., *Blood*, 104:2149-54, 2004.
Morton et al., *Arch. Surg.*, 127:392-399, 1992.

Mosier et al., *Nature*, 335:256-9, 1988.
Ody et al., *Leukemia*, 21:1285-93, 2007.
Okada and Cyster, *Curr. Opin. Immunol.*, 18:278-85, 2006.
Orlova et al., *J. Exp. Med.*, 203:2703-14, 2006.
Papayannopoulou, *Curr. Opin. Hematol.*, 10:214-9, 2003.
Pfeiffer et al., *Eur. J. Immunol.*, 38:2142-55, 2008.
Piali et al., *J. Cell. Biol.*, 130:251-60, 1995.
Qin et al., *Proc. Natl. Acad. Sci. USA*, 95(24):14411-14416, 1998.
Ravindranath and Morton, *Intern. Rev. Immunol.*, 7: 303-329, 1991.
Rosenberg et al., *Ann. Surg.*, 210(4):474-548, 1989.
Rosenberg et al., *N. Engl. J. Med.*, 319:1676, 1988.
Ruiz et al., *Cell Adhes. Commun.*, 1:67-81, 1993.
Sacharidou et al., *Blood*, 115:5259-69, 2010.
Schier et al., *Gene*, 169(2):147-155, 1996.
Spiegel et al., *Blood*, 103:2900-7, 2004.
Stemmer, *Nature*, 370:389-391, 1994.
Tavor et al., *Cancer Res.*, 64:2817-24, 2004.
Weber et al., *Nat. Rev. Immunol.*, 7:467-77, 2007.
Zen et al., *Mol. Biol. Cell.*, 16:2694-703, 2005.

What is claimed is:

1. A method for decreasing long-term B-cell lymphoma engraftment in a patient having a JAM-C positive B-cell lymphoma comprising administering an amount of a monoclonal JAM-C-binding antibody effective to decrease long-term lymphoma engraftment in the patient.

2. The method of claim 1, wherein the patient has previously been determined to have a JAM-C positive B-cell lymphoma.

3. The method of claim 1, wherein the patient is determined to have a JAM-C positive B-cell lymphoma.

4. The method of claim 1, wherein the monoclonal antibody competes successfully for binding of the polypeptide with a H225, Hj20 or Hj223.3 monoclonal antibody.

5. The method of claim 1, wherein the monoclonal antibody is a humanized monoclonal antibody.

6. The method of claim 1, wherein the monoclonal antibody fragment is a Fab, Fab', Fab'-SH, F(ab')$_2$, or scFv.

7. The method of claim 1, wherein the antibody is attached to an agent to be targeted to a JAM-C-expressing cell.

8. The method of claim 7, wherein the agent is a cytotoxic agent, a cytokine, an anti-angiogenic agent, a chemotherapeutic agent, a diagnostic agent, an imaging agent, a radioisotope, a pro-apoptosis agent, an enzyme, a hormone, a growth factor, a peptide, a protein, an antibiotic, an antibody, a Fab fragment of an antibody, an antigen, a survival factor, an anti-apoptotic agent, a hormone antagonist, a virus, a bacteriophage, a bacterium, a liposome, a microparticle, a magnetic bead, a microdevice, a cell, a nucleic acid, or an expression vector.

9. The method of claim 4, wherein the monoclonal antibody comprises the CDR sequences of the H225, Hj223.3 or Hj20 monoclonal antibody.

10. The method of claim 9, wherein the monoclonal antibody comprises:
(a) a first $V_H$ CDR is identical to SEQ ID NO: 12;
(b) a second $V_H$ CDR is identical to SEQ ID NO: 13;
(c) a third $V_H$ CDR is identical to SEQ ID NO: 14;
(d) a first $V_L$ CDR is identical to SEQ ID NO: 15;
(e) a second $V_L$ CDR is identical to SEQ ID NO: 16; and
(f) a third $V_L$ CDR is identical to SEQ ID NO: 17.

11. The method of claim 9, wherein the monoclonal antibody comprises:
(a) a first $V_H$ CDR is identical to SEQ ID NO: 24;
(b) a second $V_H$ CDR is identical to SEQ ID NO: 13;
(c) a third $V_H$ CDR is identical to SEQ ID NO: 25;
(d) a first $V_L$ CDR is identical to SEQ ID NO: 15;

(e) a second V$_L$ CDR is identical to SEQ ID NO: 16; and
(f) a third V$_L$ CDR is identical to SEQ ID NO: 17.

12. The method of claim 4, wherein the monoclonal antibody comprises:
(a) a first V$_H$ CDR is identical to SEQ ID NO: 18;
(b) a second V$_H$ CDR is identical to SEQ ID NO: 19;
(c) a third V$_H$ CDR is identical to SEQ ID NO: 20;
(d) a first V$_L$ CDR is identical to SEQ ID NO: 21;
(e) a second V$_L$ CDR is identical to SEQ ID NO: 22; and
(f) a third V$_L$ CDR is identical to SEQ ID NO: 23.

* * * * *

SEQUENCE LISTING

<160> NUMBER OF SEQ ID NOS: 34

<210> SEQ ID NO 1
<211> LENGTH: 747
<212> TYPE: DNA
<213> ORGANISM: Homo sapien
<220> FEATURE:
<221> NAME/KEY: misc_feature
<222> LOCATION: (15)..(15)
<223> OTHER INFORMATION: n is a, c, g, or t

<400> SEQUENCE: 1

```
atggcgctga ggcgnccacc gcgactccgg ctctgcgctc ggctgcctga cttcttcctg      60
ctgctgcttt tcaggggctg cctgataggg gctgtaaatc tcaaatccag caatcgaacc     120
ccagtggtac aggaatttga aagtgtggaa ctgtcttgca tcattacgga ttcgcagaca     180
agtgacccca ggatcgagtg gaagaaaatt caagatgaac aaaccacata tgtgtttttt     240
gacaacaaaa ttcagggaga cttggcgggt cgtgcagaaa tactggggaa gacatccctg     300
aagatctgga atgtgacacg gagagactca gcccttatc gctgtgaggt cgttgctcga     360
aatgaccgca aggaaattga tgagattgtg atcgagttaa ctgtgcaagt gaagccagtg     420 accctgtct gtagagtgcc gaaggctgta ccagtaggca gatggcaac actgcactgc     480 caggagagtg agggccaccc ccggcctcac tacagctggt atcgcaatga tgtaccactg     540
cccacggatt ccagagccaa tcccagattt cgcaattctt ctttccactt aaactctgaa     600
acaggcactt tggtgttcac tgctgttcac aaggacgact ctgggcagta ctactgcatt     660
gcttccaatg acgcaggctc agccaggtgt gaggagcagg agatggaagt ctctagaggg     720
cccgactaca aggacgacga tgacaag                                         747
```

<210> SEQ ID NO 2
<211> LENGTH: 249
<212> TYPE: PRT
<213> ORGANISM: Homo sapien

<400> SEQUENCE: 2

```
Met Ala Leu Arg Arg Pro Pro Arg Leu Arg Leu Cys Ala Arg Leu Pro
1               5                   10                  15

Asp Phe Phe Leu Leu Leu Leu Phe Arg Gly Cys Leu Ile Gly Ala Val
                20                  25                  30

Asn Leu Lys Ser Ser Asn Arg Thr Pro Val Val Gln Glu Phe Glu Ser
            35                  40                  45

Val Glu Leu Ser Cys Ile Ile Thr Asp Ser Gln Thr Ser Asp Pro Arg
        50                  55                  60

Ile Glu Trp Lys Lys Ile Gln Asp Glu Gln Thr Thr Tyr Val Phe Phe
65                  70                  75                  80

Asp Asn Lys Ile Gln Gly Asp Leu Ala Gly Arg Ala Glu Ile Leu Gly
                85                  90                  95
```

```
Lys Thr Ser Leu Lys Ile Trp Asn Val Thr Arg Arg Asp Ser Ala Leu
                100                 105                 110

Tyr Arg Cys Glu Val Val Ala Arg Asn Asp Arg Lys Glu Ile Asp Glu
            115                 120                 125

Ile Val Ile Glu Leu Thr Val Gln Val Lys Pro Val Thr Pro Val Cys
        130                 135                 140

Arg Val Pro Lys Ala Val Pro Val Gly Lys Met Ala Thr Leu His Cys
145                 150                 155                 160

Gln Glu Ser Glu Gly His Pro Arg Pro His Tyr Ser Trp Tyr Arg Asn
                165                 170                 175

Asp Val Pro Leu Pro Thr Asp Ser Arg Ala Asn Pro Arg Phe Arg Asn
            180                 185                 190

Ser Ser Phe His Leu Asn Ser Glu Thr Gly Thr Leu Val Phe Thr Ala
        195                 200                 205

Val His Lys Asp Asp Ser Gly Gln Tyr Tyr Cys Ile Ala Ser Asn Asp
    210                 215                 220

Ala Gly Ser Ala Arg Cys Glu Glu Gln Glu Met Glu Val Ser Arg Gly
225                 230                 235                 240

Pro Asp Tyr Lys Asp Asp Asp Lys
                245

<210> SEQ ID NO 3
<211> LENGTH: 238
<212> TYPE: PRT
<213> ORGANISM: Homo sapien

<400> SEQUENCE: 3

Met Ala Arg Arg Ser Arg His Arg Leu Leu Leu Leu Leu Leu Arg Tyr
1               5                   10                  15

Leu Val Val Ala Leu Gly Tyr His Lys Ala Tyr Gly Phe Ser Ala Pro
            20                  25                  30

Lys Asp Gln Gln Val Val Thr Ala Val Glu Tyr Gln Glu Ala Ile Leu
        35                  40                  45

Ala Cys Lys Thr Pro Lys Lys Thr Val Ser Ser Arg Leu Glu Trp Lys
50                  55                  60

Lys Leu Gly Arg Ser Val Ser Phe Val Tyr Tyr Gln Gln Thr Leu Gln
65                  70                  75                  80

Gly Asp Phe Lys Asn Arg Ala Glu Met Ile Asp Phe Asn Ile Arg Ile
                85                  90                  95

Lys Asn Val Thr Arg Ser Asp Ala Gly Lys Tyr Arg Cys Glu Val Ser
            100                 105                 110

Ala Pro Ser Glu Gln Gly Gln Asn Leu Glu Glu Asp Thr Val Thr Leu
        115                 120                 125

Glu Val Leu Val Ala Pro Ala Val Pro Ser Cys Glu Val Pro Ser Ser
    130                 135                 140

Ala Leu Ser Gly Thr Val Val Glu Leu Arg Cys Gln Asp Lys Glu Gly
145                 150                 155                 160

Asn Pro Ala Pro Glu Tyr Thr Trp Phe Lys Asp Gly Ile Arg Leu Leu
                165                 170                 175

Glu Asn Pro Arg Leu Gly Ser Gln Ser Thr Asn Ser Ser Tyr Thr Met
            180                 185                 190

Asn Thr Lys Thr Gly Thr Leu Gln Phe Asn Thr Val Ser Lys Leu Asp
        195                 200                 205

Thr Gly Glu Tyr Ser Cys Glu Ala Arg Asn Ser Val Gly Tyr Arg Arg
```

```
                210                 215                 220
Cys Pro Gly Lys Arg Met Gln Val Asp Asp Leu Asn Ile Ser
225                 230                 235

<210> SEQ ID NO 4
<211> LENGTH: 118
<212> TYPE: PRT
<213> ORGANISM: Homo sapiens

<400> SEQUENCE: 4

Gln Val Gln Leu Gln Gln Ser Gly Ala Glu Leu Ala Lys Pro Gly Ser
1               5                   10                  15

Ser Val Lys Ile Ser Cys Lys Ala Ser Gly Tyr Thr Phe Thr Ser Phe
                20                  25                  30

Tyr Ile Asn Trp Leu Lys Gln Thr Thr Gly Gln Gly Leu Glu Tyr Ile
            35                  40                  45

Gly Tyr Ile Asn Thr Gly Ser Gly Gly Thr Asn Tyr Asn Glu Lys Phe
        50                  55                  60

Lys Gly Lys Ala Thr Leu Thr Val Asp Lys Ser Ser Ser Thr Ala Phe
65                  70                  75                  80

Met Gln Leu Ser Ser Leu Thr Pro Asp Asp Ser Ala Val Tyr Tyr Cys
                85                  90                  95

Ala Arg Asp Asn Ser Gly Tyr Val Leu Asp Tyr Trp Gly Gln Gly Val
                100                 105                 110

Met Val Thr Val Ser Ser
        115

<210> SEQ ID NO 5
<211> LENGTH: 107
<212> TYPE: PRT
<213> ORGANISM: Artificial Sequence
<220> FEATURE:
<223> OTHER INFORMATION: Synthetic peptide

<400> SEQUENCE: 5

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asn Arg Tyr
                20                  25                  30

Leu Asn Trp Tyr Gln Glu Lys Val Gly Glu Ala Pro Lys Leu Leu Ile
            35                  40                  45

Tyr Asn Ala Asn Ser Leu Gln Thr Gly Ile Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asn Val Ala Thr Tyr Phe Cys Leu Gln Tyr Asn Ser Trp Pro Leu
                85                  90                  95

Thr Phe Gly Ser Gly Thr Lys Leu Glu Ile Lys
            100                 105

<210> SEQ ID NO 6
<211> LENGTH: 115
<212> TYPE: PRT
<213> ORGANISM: Artificial Sequence
<220> FEATURE:
<223> OTHER INFORMATION: Synthetic peptide

<400> SEQUENCE: 6

Gln Val Gln Leu Gln Gln Ser Gly Ala Glu Leu Val Lys Pro Gly Ser
```

-continued

```
                1               5                  10                  15
Ser Val Lys Ile Ser Cys Lys Ala Ser Gly Tyr Thr Phe Thr Ser Tyr
                20                  25                  30

Asp Met His Trp Ile Lys Gln Gln Pro Gly Asn Gly Leu Glu Trp Ile
                35                  40                  45

Gly Trp Ile Tyr Pro Gly Asn Gly Asn Thr Arg Tyr Asn Gln Lys Phe
    50                  55                  60

Asn Gly Lys Ala Thr Leu Thr Ala Asp Lys Ser Ser Thr Ala His
65                  70                  75                  80

Met Gln Leu Gly Ser Leu Thr Ser Glu Asp Ser Ala Val Tyr Phe Cys
                85                  90                  95

Ala Arg Gly Asp Gly Val Asp Tyr Trp Gly Gln Gly Val Met Val Thr
                100                 105                 110

Val Ser Ser
        115
```

<210> SEQ ID NO 7
<211> LENGTH: 106
<212> TYPE: PRT
<213> ORGANISM: Artificial Sequence
<220> FEATURE:
<223> OTHER INFORMATION: Synthetic peptide

<400> SEQUENCE: 7

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Ile Asn Lys Tyr
                20                  25                  30

Leu Asn Trp Tyr Gln Gln Lys Leu Gly Glu Ala Pro Lys Arg Leu Ile
                35                  40                  45

Tyr Lys Thr Asn Ser Leu Gln Thr Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln Tyr Asn Ser Gly Pro Arg
                85                  90                  95

Thr Phe Gly Gly Gly Thr Lys Leu Glu Ile
                100                 105
```

<210> SEQ ID NO 8
<211> LENGTH: 118
<212> TYPE: PRT
<213> ORGANISM: Artificial Sequence
<220> FEATURE:
<223> OTHER INFORMATION: Synthetic peptide

<400> SEQUENCE: 8

```
Gln Val Gln Leu Gln Gln Ser Gly Ala Glu Leu Ala Lys Pro Gly Ser
1               5                   10                  15

Ser Val Lys Ile Ser Cys Lys Ala Ser Gly Tyr Thr Phe Thr Ser Tyr
                20                  25                  30

Tyr Ile Ser Trp Ile Lys Gln Thr Thr Gly Gln Gly Leu Asp Phe Ile
                35                  40                  45

Gly Tyr Ile Asn Thr Gly Ser Gly Gly Thr Asn Tyr Asn Glu Lys Phe
        50                  55                  60

Lys Gly Lys Ala Thr Leu Thr Val Asp Lys Ser Ser Asn Thr Ala Phe
65                  70                  75                  80
```

```
Met Gln Leu Ser Ser Leu Thr Pro Asp Asp Ser Ala Val Tyr Tyr Cys
                85                  90                  95

Ala Arg Asp Glu Asp Thr Thr Pro Phe Asp Tyr Trp Gly Gln Gly Val
            100                 105                 110

Met Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Synthetic peptide

<400> SEQUENCE: 9

Asp Ile Gln Met Thr Gln Ser Pro Ser Phe Val Ser Ala Ser Val Gly
1               5                   10                  15

Asp Arg Val Thr Ile Asn Cys Lys Ala Ser Gln Asn Ile Asn Arg Tyr
            20                  25                  30

Leu Asn Trp Tyr Gln Gln Lys Leu Glu Glu Ala Pro Lys Leu Leu Ile
        35                  40                  45

Tyr Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln Tyr Asn Ser Trp Pro Leu
                85                  90                  95

Thr Phe Gly Ser Gly Thr Lys Leu Glu Ile Lys
            100                 105

<210> SEQ ID NO 10
<211> LENGTH: 118
<212> TYPE: PRT
<213> ORGANISM: Artificial Sequence
<220> FEATURE:
<223> OTHER INFORMATION: Synthetic peptide

<400> SEQUENCE: 10

Gln Val Gln Leu Gln Gln Ser Gly Ala Glu Leu Ala Lys Pro Gly Ser
1               5                   10                  15

Ser Val Lys Ile Ser Cys Lys Ala Ser Gly Tyr Thr Phe Thr Ser Tyr
            20                  25                  30

Tyr Ile Ser Trp Ile Lys Gln Thr Thr Gly Gln Gly Leu Glu Tyr Ile
        35                  40                  45

Gly Phe Ile Ser Thr Gly Ser Gly Ser Ala Asn Tyr Asn Glu Lys Phe
    50                  55                  60

Lys Gly Lys Ala Thr Phe Thr Val Asp Lys Ser Ser Thr Ala Phe
65                  70                  75                  80

Met Gln Leu Ser Ser Leu Arg Pro Asp Asp Ser Ala Val Tyr Tyr Cys
                85                  90                  95

Ala Arg Arg Asp Thr Ile Ala Val Leu Ala Tyr Trp Gly Gln Gly Thr
            100                 105                 110

Leu Val Thr Val Ser Ser
        115

<210> SEQ ID NO 11
<211> LENGTH: 106
<212> TYPE: PRT
<213> ORGANISM: Artificial Sequence
```

<220> FEATURE:
<223> OTHER INFORMATION: Synthetic peptide

<400> SEQUENCE: 11

Asp Ile Val Leu Thr Gln Ser Pro Ala Leu Ala Val Ser Pro Gly Glu
1               5                   10                  15

Arg Val Thr Ile Ser Cys Arg Ala Ser Glu Ser Val Ser Thr Leu Met
            20                  25                  30

His Trp Tyr Gln Gln Lys Pro Gly Gln Gln Pro Lys Leu Leu Ile Tyr
        35                  40                  45

Leu Ala Ser His Leu Glu Ser Gly Val Pro Ala Lys Phe Ser Gly Ser
    50                  55                  60

Gly Ser Gly Thr Asp Phe Thr Leu Thr Ile Asp Pro Val Glu Ala Asp
65                  70                  75                  80

Asp Thr Ala Thr Tyr Tyr Cys His Gln Ser Trp Asn Asp Pro Tyr Thr
                85                  90                  95

Phe Gly Ala Gly Thr Lys Leu Glu Leu Lys
            100                 105

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Gly Tyr Thr Phe Thr Ser Phe Tyr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Ile Asn Thr Gly Ser Gly Gly Thr
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Ala Arg Asp Asn Ser Gly Tyr Val Leu Asp Tyr
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Gln Asn Ile Asn Arg Tyr
1               5

```
<210> SEQ ID NO 16
<211> LENGTH: 3
<212> TYPE: PRT
<213> ORGANISM: Artificial Sequence
<220> FEATURE:
<223> OTHER INFORMATION: Synthetic peptide

<400> SEQUENCE: 16

Asn Ala Asn
1

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Leu Gln Tyr Asn Ser Trp Pro Leu Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Gly Tyr Thr Phe Thr Ser Tyr Asp
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide

<400> SEQUENCE: 19

Ile Tyr Pro Gly Asn Gly Asn Thr
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

<400> SEQUENCE: 20

Ala Arg Gly Asp Gly Val Asp Tyr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Gln Asn Ile Asn Lys Tyr
1               5

<210> SEQ ID NO 22
```

```
<211> LENGTH: 3
<212> TYPE: PRT
<213> ORGANISM: Artificial Sequence
<220> FEATURE:
<223> OTHER INFORMATION: Synthetic peptide

<400> SEQUENCE: 22

Lys Thr Asn
1

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Phe Gln Tyr Asn Ser Gly Pro Arg Thr
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Gly Tyr Thr Phe Thr Ser Tyr Tyr
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide

<400> SEQUENCE: 25

Ala Arg Asp Glu Asp Thr Thr Pro Phe Asp Tyr
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26

Ile Ser Thr Gly Ser Gly Ser Ala
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide

<400> SEQUENCE: 27

Ala Arg Arg Asp Thr Ile Ala Val Leu Ala Tyr
1               5                   10

<210> SEQ ID NO 28
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 28

Cys Arg Ala Ser Glu Ser Val Ser Thr Leu
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Synthetic peptide

<400> SEQUENCE: 29

Leu Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide

<400> SEQUENCE: 30

His Gln Ser Trp Asn Asp Pro Tyr Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X is Phe, Tyr or Trp
<220> FEATURE:
<221> NAME/KEY: MISC_FEATURE
<222> LOCATION: (8)..(8)
<223> OTHER INFORMATION: Tyr or Asp

<400> SEQUENCE: 31

Gly Tyr Thr Phe Thr Ser Xaa Xaa
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is Asn or Tyr
<220> FEATURE:
<221> NAME/KEY: MISC_FEATURE
<222> LOCATION: (3)..(3)
<223> OTHER INFORMATION: X isThr or Pro
<220> FEATURE:
<221> NAME/KEY: MISC_FEATURE
<222> LOCATION: (5)..(5)
<223> OTHER INFORMATION: X is Ser or Asn
<220> FEATURE:
<221> NAME/KEY: MISC_FEATURE
<222> LOCATION: (7)..(7)
```

```
<223> OTHER INFORMATION: X is Gly or Asn

<400> SEQUENCE: 32

Ile Xaa Xaa Gly Xaa Gly Xaa Thr
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X is Arg, His or Lys

<400> SEQUENCE: 33

Gln Asn Ile Asn Xaa Tyr
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is Phe or Leu
<220> FEATURE:
<221> NAME/KEY: MISC_FEATURE
<222> LOCATION: (6)..(6)
<223> OTHER INFORMATION: X9 is Gly or Trp
<220> FEATURE:
<221> NAME/KEY: MISC_FEATURE
<222> LOCATION: (8)..(8)
<223> OTHER INFORMATION: X10 is Arg or Leu

<400> SEQUENCE: 34

Xaa Gln Tyr Asn Ser Xaa Pro Xaa Thr
1               5
```